United States Patent
Smith et al.

(10) Patent No.: US 8,629,169 B2
(45) Date of Patent: Jan. 14, 2014

(54) 4-SUBSTITUTED-3-PHENYLSULFANYL-METHYL-BICYCLO[3.1.0]HEXANE COMPOUNDS AS MGLUR 2/3 ANTAGONISTS

(75) Inventors: Stephon Cornell Smith, Fishers, IN (US); Renhua Li, Fishers, IN (US); Charles Howard Mitch, Columbus, IN (US); Tatiana Natali Vetman, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 114 days.

(21) Appl. No.: 13/296,384

(22) Filed: Nov. 15, 2011

(65) Prior Publication Data

US 2012/0129902 A1 May 24, 2012

Related U.S. Application Data

(60) Provisional application No. 61/415,121, filed on Nov. 18, 2010.

(51) Int. Cl.
| | |
|---|---|
| *A61K 31/4196* | (2006.01) |
| *A61K 31/216* | (2006.01) |
| *A61K 31/196* | (2006.01) |
| *C07D 249/12* | (2006.01) |
| *C07C 69/96* | (2006.01) |
| *C07C 69/757* | (2006.01) |
| *C07C 69/753* | (2006.01) |
| *C07C 321/28* | (2006.01) |

(52) U.S. Cl.
USPC ........ 514/384; 514/510; 514/562; 548/264.2; 558/267; 560/18; 562/432

(58) Field of Classification Search
None
See application file for complete search history.

(56) References Cited

U.S. PATENT DOCUMENTS

| | | | |
|---|---|---|---|
| 5,916,920 | A | 6/1999 | Fernandez et al. |
| 6,107,342 | A | 8/2000 | Adam et al. |
| 7,157,594 | B2 | 1/2007 | Nakazato et al. |
| 7,381,746 | B2 | 6/2008 | Yasuhara et al. |
| 2006/0142388 | A1 | 6/2006 | Yasuhara et al. |
| 2007/0021394 | A1 | 1/2007 | Yasuhara et al. |

FOREIGN PATENT DOCUMENTS

| | | |
|---|---|---|
| EP | 0774455 A1 | 5/1997 |
| EP | 1897550 A2 | 3/2008 |
| JP | 339199 | 12/2004 |
| JP | 193507 | 7/2006 |
| WO | 99/47490 | 9/1999 |
| WO | 00/04010 A1 | 1/2000 |
| WO | 2005/000789 A1 | 1/2005 |

OTHER PUBLICATIONS

Dominguez, et al., Asymmetric synthesis of (+)-2-aminobicyclo[3.1.0]hexane-2,6-dicarboxylic acid (LY354740), Tetrahedron: Asymmetry, vol. 8, No. 4: 511-514, (1997).
Li, et al., Metabotropic Glutamate 5 Receptor Antagonism Is Associated with Antidepressant-Like Effects in Mice, The J. of Pharmacology and Experimental Therapeutics, vol. 319: 1, 254-259 (2006).
Yasuhara, et al., Metabotropic Glutamate Receptors: Potential Drug Targets for Psychiatric Disorders, The Open Med. Chemistry Journal, 4: 20-36 (2010).
Kuo, et al., Synthesis of LY455169-2H2, A Model Study for the Trituium Labeling of LY459477. 2. Synthesis of LY459477-[3H2], Synthesis and Applications of Isotopically Labelled Compounds, vol. 8 (2004).
Yasuhara, et al., Synthesis, in vitro pharmacology, and structure-activity relationships of 2-aminobicyclo[3.1.0] hexane-2,6-dicarboxylic acid derivatives as mGluR2 antagonists, Bioorganic & Medicinal Chemistry 14: 3405-3420 (2006).
Sakagami, et al., Synthesis, in vitro pharmacology, and pharmacokinetic profiles of 2-[1-amino-1-carboxy-2-(9H-xanthen-9-yl)ethyl]-1-fluoro-cyclopropanecarboxylic acid and its 6-heptyl ester, a potent mGluR2 antagonist Bioorganic & Medicinal Chemistry 16: 4359-4366 (2008).
Nakazato, et al., Synthesis SARs, and Pharmacological Characterization of 2-Amino-3 or 6-fluorobicyclo[3.1.0] hexane-2,6-dicarboxylic Acid Derivatives as Potent, Selective, and Orally Active Group II Metabotropic Glutamate Receptor Agonists, J. Med. Chem., 43: 4893-4909 (2000).
Dominguez, et al., Enantiospecific synthesis of (1S,2S,5R,6S)-2-Aminobicyclo[3.1.0]hexane-2,6-dicarboxylic acid by a modified Corey-Link reaction[1], Tetrahedron Letters 39: 9305-9308 (1998).
Witkin, et al., Antagonism of Metabotropic Glutamate Group II Receptors in the Potential Treatment of Neurological and Neuropsychiatric Disorders, Drug Development Research 67: 757-769 (2006).
Yasuhara et al. "Prodrugs of 3-(3,4-dichlorobenzyloxy)-2-amino-6-fluorobicyclo[3.1.0]hexane-2,6-dicarboxylic acid (MGS0039): A potent and orally active group II mGluR antagonist with antidepressant-like potential" Bioorganic & Medicinal Chemistry 14 (2006) 4193-4207.

*Primary Examiner* — Alicia L Otton
(74) *Attorney, Agent, or Firm* — R. Craig Tucker

(57) ABSTRACT

A mGlu2/3 receptor antagonist of the formula:

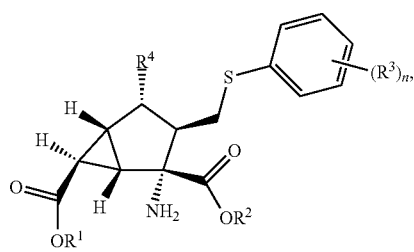

its uses, and methods for its preparation are described.

24 Claims, No Drawings

4-SUBSTITUTED-3-PHENYLSULFANYL-METHYL-BICYCLO[3.1.0]HEXANE COMPOUNDS AS MGLUR 2/3 ANTAGONISTS

This application claims priority to U.S. provisional application Ser. No. 61/415,121, filed Nov. 18, 2010.

Glutamate is the major excitatory neurotransmitter in the brain and is involved in a wide variety of physiological processes mediated through no less than 11 distinct receptors, each with its own pharmacology. Metabotropic Glutamate Receptor subtypes 2 and 3 (known as mGlu2 and mGlu3) are often grouped together as Group II mGlu receptors based on their sequence homology, similar second messenger coupling, and similar pharmacological characteristics. Antagonists of mGlu2/3 receptors have exhibited significant pharmacological effects in animal models for depressive disorders and disorders of excessive sleepiness. As such, mGlu2/3 antagonists are deemed to be useful in the treatment of depressive disorders such as major depressive disorder (MDD), unipolar depression, dysthymia, and/or cyclothymia, and/or useful in the treatment of disorders of excessive sleepiness, such as excessive daytime sleepiness (EDS), hypersomnia associated with obstructive sleep apnea or narcolepsy, circadian rhythm sleep disorders (including, but not limited to shift work sleep disorder, jet lag disorder, delayed sleep phase disorder, advanced phase sleep disorder, and non-24 hour sleep-wake syndrome), idiopathic hypersomnolance and/or excessive sleepiness associated with non-restorative sleep (NRS).

U.S. Pat. No. 5,916,920 describes certain 3-monosubstituted bicyclo[3.1.0]hexane compounds as metabotropic glutamate receptor modulators useful for treating a variety of disorders including as antidepressant agents. U.S. Pat. No. 7,157,594 describes various 3-monosubstituted bicyclo[3.1.0]hexane compounds as Group II mGlu receptor antagonists for use in treating various disorders including depressive symptoms. US 2007/0021394 A1 describes various 3-monosubstituted bicyclo[3.1.0]hexane compounds as Group II mGlu receptor antagonists and prodrugs thereof for use in treating various disorders including depression.

The present invention provides a family of 4-substituted-3-phenylsulfanylmethyl-bicyclo[3.1.0]hexane compounds with high antagonist potency for the mGlu2 and mGlu3 receptors. The compounds of the present invention are also selective for the mGlu2 and mGlu3 receptors, particular as against other mGlu receptors. Certain compounds have also demonstrated through animal models that the compounds of the present invention may be useful for the treatment of depressive disorders (which may include major depressive disorder (MDD), unipolar depression, dysthymia, and/or cyclothymia) and disorders of excessive sleepiness (which may include excessive daytime sleepiness (EDS), hypersomnia associated with obstructive sleep apnea or narcolepsy, circadian rhythm sleep disorders (including, but not limited to shift work sleep disorder, jet lag disorder, delayed sleep phase disorder, advanced phase sleep disorder, and non-24 hour sleep-wake syndrome), idiopathic hypersomnolance and/or excessive sleepiness associated with non-restorative sleep (NRS)). The antidepressant-like and wake-promoting effects of this mechanism also predict impact on symptoms of depressive disorders such as fatigue that are otherwise difficult to treat with existing antidepressants.

The present invention provides compounds of Formula I:

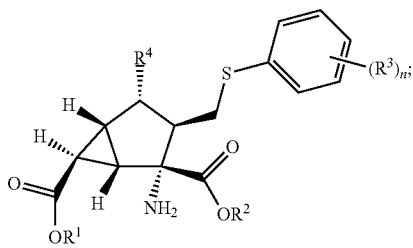

where $R^1$ and $R^2$ are each independently hydrogen, $C_1$-$C_3$ alkoxycarbonyloxymethyl, $C_1$-$C_5$ alkylcarbonyloxymethyl, or $C_{3-6}$ cycloalkylcarbonyloxymethyl;
$R^3$ is independently at each occurrence methyl, fluoro, or chloro;
$R^4$ is hydroxyl, amino, methylcarbonylamino, or 1,2,4-triazolylthio; and
n is 1 or 2;
or a pharmaceutically acceptable salt thereof.

It is a feature of the present invention that compounds of Formula I wherein $R^1$ and $R^2$ are both hydrogen (the di-acid compounds) are the therapeutically active compounds in vivo, whereas compounds where $R^1$ or $R^2$ or both are other than hydrogen are prodrugs of their therapeutically active di-acid analogs. The compounds where $R^1$ or $R^2$ or both are other than hydrogen are hydrolyzed in vivo to provide the therapeutically active di-acid analog. The prodrug compounds when administered orally, particularly di-ester prodrugs, provide improved bioavailability of the di-acid metabolite compared to oral administration of the di-acid compounds ($R^1$ and $R^2$ both hydrogen), but the di-acid compounds provide better activities when administered intravenously, intramuscularly or subcutaneously.

In another aspect of the invention there is provided a pharmaceutical composition comprising a compound of Formula I or a pharmaceutically acceptable salt thereof, in combination with at least one pharmaceutically acceptable carrier, diluent, or excipient. Furthermore, this aspect of the invention provides a pharmaceutical composition adapted for the treatment of depressive disorders, as for example major depressive disorder, unipolar depression, dysthymia, and/or cyclothymia, comprising a compound of Formula I or a pharmaceutically acceptable salt thereof, in combination with one or more pharmaceutically acceptable excipients, carriers, or diluents thereof.

A further embodiment of this aspect of the invention provides a pharmaceutical composition comprising a compound according to Formula I, or pharmaceutically acceptable salt thereof, in combination with at least one pharmaceutically acceptable carrier, excipient or diluents, and optionally other therapeutic ingredients. In a yet further embodiment of this aspect of the invention, the pharmaceutical composition further comprises a second therapeutic agent which is a drug useful in the treatment of depressive disorders, as for example a serotonin reuptake inhibitor, as for example fluoxetine and/or citalopram.

In yet another embodiment of this aspect of the invention there is provided a pharmaceutical composition adapted for the treatment of disorders of excessive sleepiness, as for example, excessive daytime sleepiness (EDS), hypersomnia associated with obstructive sleep apnea or narcolepsy, circadian rhythm sleep disorders (including, but not limited to shift work sleep disorder, jet lag disorder, delayed sleep phase disorder, advanced phase sleep disorder, and non-24 hour sleep-wake syndrome), idiopathic hypersomnolance and/or excessive sleepiness associated with non-restorative sleep (NRS), comprising a compound of Formula I or a pharmaceutically acceptable salt thereof, in combination with one or more pharmaceutically acceptable excipients, carriers, or diluents thereof.

The present invention also provides a method of treating depressive disorders, as for example major depressive disorder (MDD), unipolar depression, dysthymia, and/or cyclothymia, in a mammal comprising administering to a mammal in need of such treatment an effective amount of a compound of Formula I or a pharmaceutically acceptable salt thereof. In another embodiment of this aspect of the invention, the method further comprises administering in simultaneous, separate or sequential combination, a second therapeutic agent which is a drug useful in the treatment of depressive disorders, as for example a serotonin reuptake inhibitor, as for example fluoxetine and/or citalopram.

Other embodiments of the invention provide methods of treating disorders of excessive sleepiness comprising administering to a mammal in need of such treatment an effective amount of a compound of Formula I, or a pharmaceutically acceptable salt thereof. In other embodiments of this aspect of the invention, the excessive sleepiness is due to any one or more of the following: excessive daytime sleepiness (EDS), hypersomnia associated with obstructive sleep apnea or narcolepsy, circadian rhythm sleep disorders (including, but not limited to shift work sleep disorder, jet lag disorder, delayed sleep phase disorder, advanced phase sleep disorder, and non-24 hour sleep-wake syndrome), idiopathic hypersomnolance or excessive sleepiness associated with non-restorative sleep (NRS).

In one particular embodiment of these methods of treatment, the mammal is a human.

This invention also provides a compound of Formula I or a pharmaceutically acceptable salt thereof for use in therapy. Within this aspect, the invention provides a compound of Formula I, or a pharmaceutically acceptable salt thereof, for use in the treatment of depressive disorders. In further embodiments, the depressive disorder is any one of major depressive disorder (MDD), unipolar depression, dysthymia, and/or cyclothymia. In another embodiment of this aspect of the invention, the invention provides a compound according to Formula I, or a pharmaceutically acceptable salt thereof, for use in simultaneous, separate or sequential combination with a serotonin reuptake inhibitor, as for example fluoxetine and/or citalopram, in the treatment of depressive disorders.

Further, this aspect of the invention includes a compound of Formula I, or a pharmaceutically acceptable salt thereof, for use in the treatment of disorders of excessive sleepiness. In particular embodiments of this aspect of the invention, the excessive sleepiness is due to any one or more of the following: excessive daytime sleepiness (EDS), hypersomnia associated with obstructive sleep apnea or narcolepsy, circadian rhythm sleep disorders (including, but not limited to shift work sleep disorder, jet lag disorder, delayed sleep phase disorder, advanced phase sleep disorder, and non-24 hour sleep-wake syndrome), idiopathic hypersomnolance or excessive sleepiness associated with non-restorative sleep (NRS).

One particular embodiment of this aspect of the inventions, the uses are in mammals, particular humans.

Another aspect of this invention provides the use of a compound of Formula I, or a pharmaceutically acceptable salt thereof, in the manufacture of a medicament for the treatment of depressive disorders, as for example major depressive disorder (MDD), unipolar depression, dysthymia, and/or cyclothymia. Another embodiment of this aspect of the invention provides the use of a compound of Formula I, or a pharmaceutically acceptable salt thereof, and a second therapeutic agent useful in the treatment of depressive disorders, as for example a serotonin reuptake inhibitor, as for example fluoxetine and/or citalopram, in the manufacture of a medicament for the treatment of depressive disorders. Another embodiment of the invention provides the use of a compound of Formula I, or a pharmaceutically acceptable salt thereof, in the manufacture of a medicament for the treatment of disorders of excessive sleepiness. In particular embodiments of this aspect of the invention, the medicament is for the treatment of any one or more of the following: excessive daytime sleepiness (EDS), hypersomnia associated with obstructive sleep apnea or narcolepsy, circadian rhythm sleep disorders (including, but not limited to shift work sleep disorder, jet lag disorder, delayed sleep phase disorder, advanced phase sleep disorder, and non-24 hour sleep-wake syndrome), idiopathic hypersomnolance or excessive sleepiness associated with non-restorative sleep (NRS).

Compounds of this invention have basic and acidic moieties, and accordingly react with a number of organic and inorganic acids and bases to form pharmaceutically acceptable salts. Pharmaceutically acceptable salts of each of the compounds of the present invention are contemplated within the scope of the present application. The term "pharmaceutically acceptable salt" as used herein, refers to any salt of a compound of the invention that is substantially non-toxic to living organisms. Such salts include those listed in *Journal of Pharmaceutical Science*, 66, 2-19 (1977), which are known to the skilled artisan.

Preferred classes of compounds of the present invention are compounds wherein:
1) $R^1$ and $R^2$ are both hydrogen;
2) $R^1$ or $R^2$ or both are other than hydrogen;
3) $R^1$ and $R^2$ are both other than hydrogen;
4) $R^1$ and $R^2$ are the same and are other than hydrogen;
5) $R^1$ and $R^2$ are each isopropoxycarbonyloxymethyl;
6) n is 2;
7) $R^3$ is independently at each occurrence fluoro or chloro;
8) n is 2 and the $R^3$ groups are at the phenyl 3- and 4-positions.
9) n is 2 and the $R^3$ groups each independently fluoro or chloro and are at the phenyl 3- and 4-positions.
10) n is 2, both $R^3$ groups are fluoro, and the fluoro groups are at the phenyl 3- and 4-positions;
11) n is 2, and the $R^3$ groups together with the phenyl moiety to which they are attached form 3-chloro-4-fluorophenyl;
12) $R^4$ is hydroxyl.

It will be understood that further preferred compounds are those combining the above preferred selections for a given substituents with preferred selections of other substituents. Examples of such combinations include, but are not limited to the following preferred classes of compounds:
13) preferred compounds of any one of paragraphs 1-5 (preferred selections for $R^1$ and $R^2$) wherein n is 2, both $R^3$ groups are fluoro, and the fluoro groups are at the phenyl 3- and 4-positions (paragraph 10);
14) preferred compounds of any one of paragraphs 1-5 (preferred selections for $R^1$ and $R^2$) wherein n is 2, and the $R^3$ groups together with the phenyl moiety to which they are attached form 3-chloro-4-fluorophenyl (paragraph 11);

15) preferred compounds of any one of paragraphs 1-5 (preferred selections for $R^1$ and $R^2$) wherein $R^4$ is hydroxyl (paragraph 12);

16) preferred compounds of any one of paragraphs 13-14 where $R^4$ is hydroxyl (paragraph 12).

Specific preferred compounds are those described in the Examples including their freebases and pharmaceutically acceptable salts thereof.

Certain preferred compounds are:

(1S,2R,3S,4S,5R,6R)-2-amino-3-{[(3,4-difluorophenyl)sulfanyl]methyl}-4-hydroxybicyclo[3.1.0]hexane-2,6-dicarboxylic acid or a pharmaceutically acceptable salt thereof;

(1S,2R,3S,4S,5R,6R)-2-Amino-3-{[(3-chloro-4-fluorophenyl)sulfanyl]methyl}-4-hydroxybicyclo[3.1.0]hexane-2,6-dicarboxylic acid, or a pharmaceutically acceptable salt thereof;

bis({[(1-methylethoxy)carbonyl]oxy}methyl)(1S,2R,3S,4S,5R,6R)-2-amino-3-{[(3,4-difluorophenyl)sulfanyl]methyl}-4-hydroxybicyclo[3.1.0]hexane-2,6-dicarboxylate; or a pharmaceutically acceptable salt thereof; and bis({[(1-methylethoxy)carbonyl]oxy}methyl)(1S,2R,3S,4S,5R,6R)-2-amino-3-{[(3-chloro-4-fluorophenyl)sulfanyl]methyl}-4-hydroxybicyclo[3.1.0]hexane-2,6-dicarboxylate, or a pharmaceutically acceptable salt thereof (i.e. the compounds of Examples 1, 2, 12, 22 and 32, and alternative pharmaceutically acceptable salts thereof).

Abbreviations used herein are defined as follows:

"BSA" means bovine serum albumin.
"DCG IV" means (2S,2'R,3'R)-2-(2',3'-dicarboxycyclopropyl)glycine.
"DMEM means Dulbecco's Minimum Eagle's Medium.
"DMSO" means dimethyl sulfoxide.
"DPBS" means Dulbecco's Phosphate Buffered Saline.
"EDTA" means ethylene diamine tetraacetic acid.
"GTP" means guanosine triphosphate.
"HBSS" means Hank's Buffered Salt Solution.
"HEPES" means 4-(2-hydroxyethyl)-1-piperazine ethanesulfonic acid.
"HPLC" means high-pressure liquid chromatography.
"IBMX" means 3-isobutyl-1-methylxanthine
"$IC_{50}$" means the concentration at which 50% of the maximum inhibition is achieved.
"i.v." means intravenous or intravenously.
"i.p." means intraperitoneal.
"L-AP-4" means L-(+)-2-amino-4-phosphonobutyric acid.
"LC/MS" means liquid chromatography followed by mass spectroscopy.
"mFST" means mouse forced swim test; an animal model for antidepressant activity.
"MS" means mass spectroscopy.
"MS (ES+)" means mass spectroscopy using electrospray ionization.
"NMR" means nuclear magnetic resonance.
"p.o." means per os, by mouth.
"tBu" means a tertiary-butyl moiety.

General Chemistry

The compounds of the present invention can be prepared according to the following synthetic schemes by methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of the present invention is dependent upon the particular compound being synthesized, the starting compound, and the relative liability of the substituted moieties, as is well appreciated by the skilled chemist. All substituents, unless otherwise indicated, are as previously defined, and all reagents are well known and appreciated in the art.

Prodrug compound 1 may be prepared as illustrated in Scheme I where $R^1$, $R^2$, $R^3$, $R^4$, and n are as previously defined, and $R^1$ and $R^2$ are not both hydrogen.

Scheme I

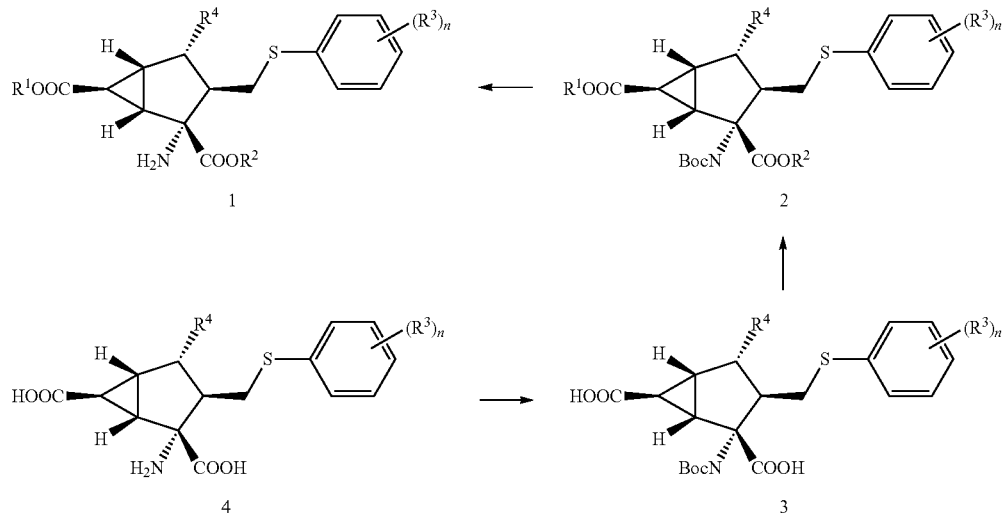

Compound 4 is reacted with an amino protecting reagent such as di-tert-butyldicarbonate under conditions well known to the skilled artisan to provide the compound 3. When $R^1$ and $R^2$ group are identical in the compound 2, the compound 3 is reacted with sufficient amount of proper chloromethyl alkyl carbonate and appropriate reagents such as sodium iodide and cesium carbonate in a suitable solvent such as dimethylformamide to give the desired di-ester compound 2 with same $R^1$ and $R^2$. When $R^1$ and $R^2$ are different in the compound 2, by controlling the amount of first chloromethyl alkyl carbonate to about one equivalent, the carboxylic acid on the five-membered ring can be converted to a $R^2$ mono ester first. The $R^2$ mono ester compound can further react with one equivalent of different chloromethyl alkyl carbonate. The free carboxylic acid group on the three-membered ring can then be converted to a $R^1$ ester to provide the desired di-ester with different $R^1$ and $R^2$. To make a $R^2$ mono ester on the five membered ring of the compound 2, the compound 3 is reacted with about one equivalent of proper chloromethyl alkyl carbonate and appropriate reagents such as sodium iodide and cesium carbonate in a suitable solvent such as dimethylformamide to give the desired $R^2$ mono ester compound 2, in which $R^1$ is hydrogen. To make a $R^1$ mono ester on the three-membered ring, the carboxylic acid group on the five-membered ring should be protected first since it is more reactive under basic conditions. More specifically, the carboxylic acid group on the five-membered ring in compound 3 can react with alpha-chloro-4-methoxytoluene, sodium iodide and sodium bicarbonate in a suitable solvent such as dimethylformamide to provide a 4-methoxylbenzyl mono ester. The free carboxylic acid group on the three-membered ring of the protected 4-methoxylbenzyl mono ester compound is then reacted with a proper chloromethyl alkyl carbonate to afford a desired $R^1$ ester on the three-membered ring. The di-ester is treated with a proper acid such as trifluoroacetic acid to de-protect the 4-methoxylbenzyl and N-tert-butoxycarbonyl group to afford the desired $R^1$ mono ester compound 1, in which $R^2$ is hydrogen. The compound 2, including $R^2$ mono ester and di-ester with same or different $R^1$ and $R^2$, is then de-protected with a proper acid such as hydrochloric acid in dioxane to give the desired compound 1 or a pharmaceutically acceptable salt.

Scheme II

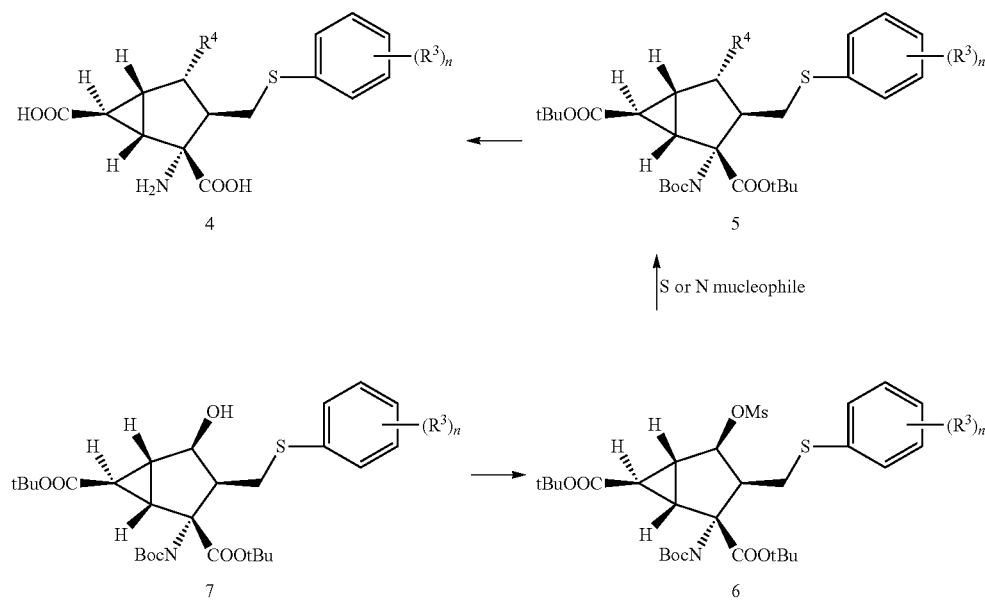

Active parent compound 4 in which $R^4$ is not a hydroxyl group may be prepared as illustrated in Scheme II.

The compound 7 is reacted with methanesulfonyl chloride and a proper base such as pyridine to give the mesylate compound 6. Compound 6 can react with thiol heterocycle such as 1H-1,2,4-triazole-3-thiol, and a suitable base such as cesium carbonate in a solvent such as dimethylformamide to give the desired compound 5, in which $R^4$ is a desired thio linked heterocycle. Compound 6 can also react with sodium azide to give an azide intermediate, which is then reduced with reducing reagent such as 1,3-propanedithiol in a suitable solvent such as methanol to provide compound 5 in which $R^4$ is an amino group. The resulted amine can further form an amide with methods well known to skilled artisans to give compound 5, in which $R^4$ is a desired amide. The compound 5 is then de-protected with proper acid such as hydrochloric acid or acetic acid to give the compound 4.

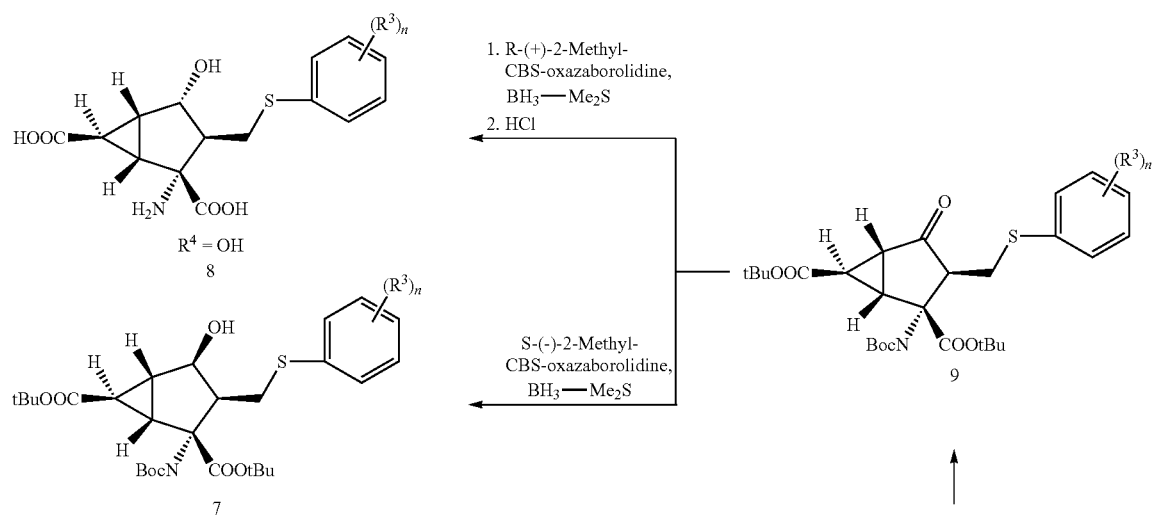

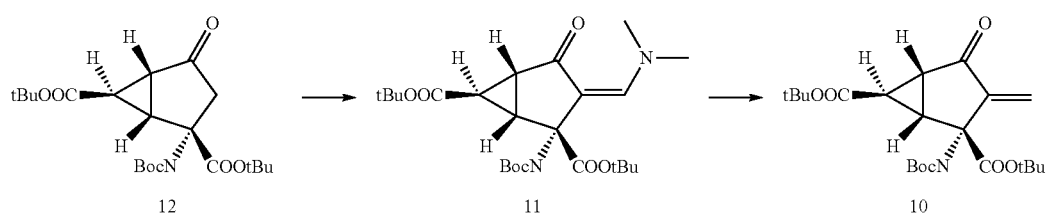

Active parent compound 8 in which $R^4$ is hydroxyl group and the key intermediate compound 7 in which $R^4$ is group other than hydroxyl group may be prepared as illustrated in Scheme III.

Compound 12 (See WO03/104217/A2 for synthesis details) is reacted with tert-butoxybis(dimethylamino)methane in toluene to provide compound 11. Compound 11 in a suitable solvent such as tetrahydrofuran is treated with a proper base such as triethylamine and a proper reducing reagent such as diisobutylaluminium hydride under lowered temperature to afford the compound 10. Compound 10 is then reacted with triethylamine and a proper substituted benzenethiol such as 3,4-difluorobenzenethiol in a suitable solvent such as toluene to afford compound 9. The ketone group of compound 9 can be selectively reduced to desired (S) hydroxyl or (R) hydroxyl compound by using (R)-methyl oxazaborolidine or (S)-methyl oxazaborolidine, respectively. The (S) hydroxyl intermediate is de-protected with a proper acid such as hydrochloric acid in a solvent such as dioxane to provide the desired active parent compound 8 in which $R^4$ is a (S) hydroxyl group. The (R) hydroxyl intermediate 7 can be converted to the desired product with the method illustrated in Scheme II.

Preparation 1: Di-tert-butyl (1S,2R,5R,6R)-2-(tert-butoxycarbonylamino)-3-(dimethylaminomethylene)-4-oxo-bicyclo[3.1.0]hexane-2,6-dicarboxylate

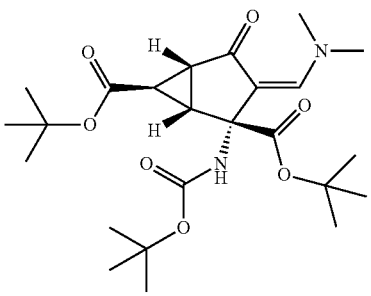 [SMILES: CN(C)/C=C1\C(=O)[C@H]2[C@H](C(=O)OC(C)(C)C)[C@H]2[C@]1(NC(=O)OC(C)(C)C)C(=O)OC(C)(C)C]

To a solution of di-tert-butyl (1S,2S,5R,6R)-2-[(tert-butoxycarbonyl)amino]-4-oxobicyclo[3.1.0]hexane-2,6-dicar boxylate (15.15 g, 36.82 mmol, See WO03/104217/A2 for synthesis details) in toluene (90.90 mL) is added tert-butoxybis(dimethylamino)methane (12.83 g, 73.63 mmol). This mixture is then heated to 80° C. for 1 hour and then allowed to cool to ambient temperature. The solvent volume is reduced to about 35 ml. The mixture is stirred while diethyl ether and hexane are added to cause a precipitate to form. The solids are collected by filtration, washed with hexanes, and air dried to obtain the title compound (16.7 g, 35.79 mmol, 97.2% yield). MS (m/z): 467.2 (M+H).

Preparation 2: Di-tert-butyl (1S,2R,5R,6R)-2-[(tert-butoxycarbonyl)amino]-3-methylidene-4-oxobicyclo[3.1.0]hexane-2,6-dicarboxylate

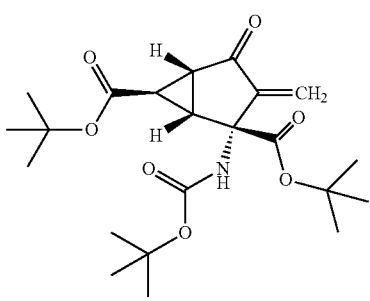 [SMILES: C=C1C(=O)[C@H]2[C@H](C(=O)OC(C)(C)C)[C@H]2[C@]1(NC(=O)OC(C)(C)C)C(=O)OC(C)(C)C]

To a solution of di-tert-butyl (1S,2R,5R,6R)-2-(tert-butoxycarbonylamino)-3-(dimethylaminomethylene)-4-oxobicyclo[3.1.0]hexane-2,6-dicarboxylate (15.7 g, 33.8 mmol) in tetrahydrofuran (340 ml) is added triethylamine (6.6 mL, 47.32 mmol). The mixture is cooled to −78° C. Diisobutylaluminium hydride (1N in toluene, 50 mL, 50 mmol) is added over one hour. The mixture is stirred for two additional hours. Then add 30 mL of saturated aqueous ammonium chloride. The mixture is allowed to warm to ambient temperature. The mixture is transferred to a separatory funnel and washed with brine. The organic layer is dried over MgSO$_4$, filtered, and concentrated under reduced pressure to give a residue. The residue is purified by flash chromatography (0 to 50% ethyl acetate/hexanes) to give the title compound (12 g, 33.34 mmol, 83.8% yield). MS (m/z): 422 (M−H).

Preparation 3: Di-tert-butyl (1S,2R,3S,4S,5R,6R)-2-[(tert-butoxycarbonyl)amino]-3-{[(3,4-difluorophenyl)sulfanyl]methyl}-4-hydroxybicyclo[3.1.0]hexane-2,6-dicarboxylate

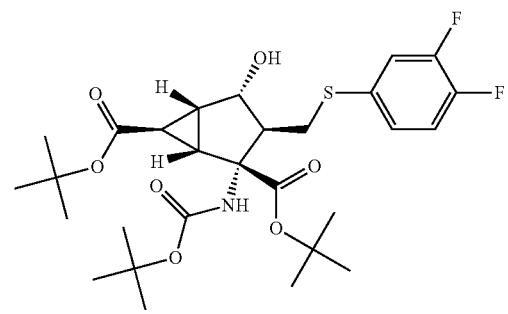 [SMILES: CC(C)(C)OC(=O)N[C@]1(C(=O)OC(C)(C)C)[C@@H]2[C@@H](C(=O)OC(C)(C)C)[C@@H]2[C@H](O)[C@H]1CSc1ccc(F)c(F)c1]

Di-tert-butyl (1S,2R,5R,6R)-2-[(tert-butoxycarbonyl)amino]-3-methylidene-4-oxobicyclo[3.1.0]hexane-2,6-dicarboxylate (1.03 g, 2.43 mmol) in diethyl ether (100 mL) is bubbled with nitrogen gas for 10 minutes. Add 3,4-difluorobenzenethiol (0.36 g, 2.43 mmol) and triethylamine (0.01 mL, 0.05 μmol). The mixture is warmed to 40° C. and stirred for 15 minutes. The mixture is then allowed to cool to ambient temperature, transferred to a separatory funnel, diluted with hexane (40 mL), washed with of 2N aqueous KOH (1×30 mL), dried over magnesium sulfate, filtered, and concentrated under reduced pressure giving di-tert-butyl (1S,2R,3S,5R,6R)-2-[(tert-butoxycarbonyl)amino]-3-{[(3,4-difluorophenyl)sulfanyl]methyl}-4-oxobicyclo[3.1.0]hexane-2,6-dicarboxylate (1.35 g, 2.37 mmol): MS (m/z): 567.8 (M−H). This material is taken up in 120 mL of diethyl ether and added slowly over 2 hours to a 200 mL ether solution at −10° C. which contains R-(+)-2-methyl-CBS-oxazaborolidine (981.72 mg, 3.54 mmol) and borane-methyl sulfide complex (2M in tetrahydrofuran, 5.02 mL, 10.04 mmol). The mixture is stirred for an additional hour after final addition of di-tert-butyl (1S,2R,3S,5R,6R)-2-[(tert-butoxycarbonyl)amino]-3-{[(3,4-difluorophenyl)sulfanyl]methyl}-4-oxobicyclo[3.1.0]hexane-2,6-dicarboxylate. Silica gel (30 g) is added over 30 minutes and the reaction mixture is gradually warmed to ambient temperature. The suspension is filtered, and washed with 300 mL of diethyl ether. The solvent is concentrated under reduced pressure giving a residue. The residue is purified by flash chromatography, eluting with (0 to 15% ethyl acetate/hexanes) to give the title compound (0.844 g, 1.48 mmol, 60.7% yield): MS (m/z): 569.8 (M−H).

The following compounds are prepared essentially by the method of Preparation 3:

| Prep. No. | Chemical Name | Structure | Yield (%) | Physical Data MS(m/z) |
|---|---|---|---|---|
| 4 | Di-tert-butyl (1S,2R,3S,4S,5R,6R)-2-[(tert-butoxycarbonyl)amino]-3-{[(3-chloro-4-fluoro-phenyl)sulfanyl]methyl}-4-hydroxybicyclo[3.1.0]hexane-2,6-dicarboxylate | 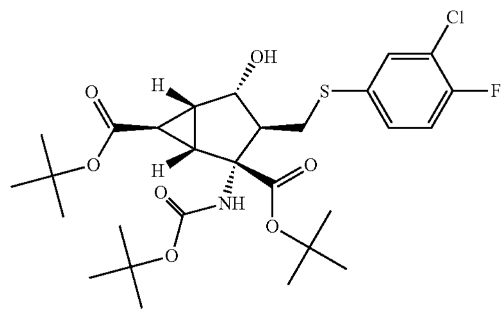 [SMILES: CC(C)(C)OC(=O)N[C@]1(C(=O)OC(C)(C)C)[C@@H]2[C@@H](C(=O)OC(C)(C)C)[C@@H]2[C@H](O)[C@H]1CSc1ccc(F)c(Cl)c1] | 84.0 | (M + H): 585.8 |
| 5 | Di-tert-butyl (1S,2R,3S,4S,5R,6R)-2-(tert-butoxycarbonylamino)-3-[(4-fluoro-3-methyl-phenyl)sulfanylmethyl]-4-hydroxy-bicyclo[3.1.0]hexane-2,6-dicarboxylate | 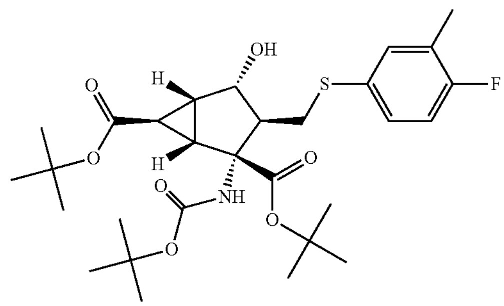 [SMILES: Cc1cc(SC[C@@H]2[C@@H](O)[C@H]3[C@H](C(=O)OC(C)(C)C)[C@H]3[C@]2(NC(=O)OC(C)(C)C)C(=O)OC(C)(C)C)ccc1F] | 73.5 | (M + Na): 590.0 |
| 6 | Di-tert-butyl (1S,2R,3S,4S,5R,6R)-2-(tert-butoxycarbonylamino)-3-[(3,4-dichlorophenyl)sulfanylmethyl]-4-hydroxy-bicyclo[3.1.0]hexane-2,6-dicarboxylate | 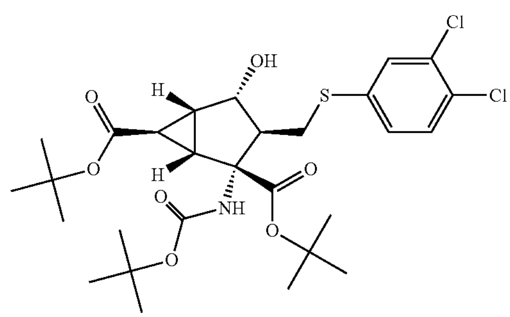 [SMILES: CC(C)(C)OC(=O)N[C@]1(C(=O)OC(C)(C)C)[C@@H]2[C@@H](C(=O)OC(C)(C)C)[C@@H]2[C@H](O)[C@H]1CSc1ccc(Cl)c(Cl)c1] | 75.2 | (M + Na): 625.8 |
| 7 | Di-tert-butyl (1S,2R,3S,4S,5R,6R)-2-(tert-butoxycarbonylamino)-3-[(3-chlorophenyl)sulfanylmethyl]-4-hydroxy-bicyclo[3.1.0]hexane-2,6-dicarboxylate | 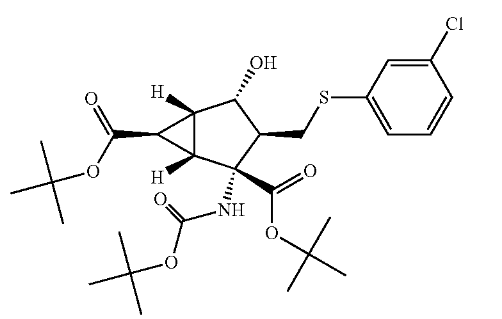 [SMILES: CC(C)(C)OC(=O)N[C@]1(C(=O)OC(C)(C)C)[C@@H]2[C@@H](C(=O)OC(C)(C)C)[C@@H]2[C@H](O)[C@H]1CSc1cccc(Cl)c1] | 82.6 | (M − H): 567.8 |
| 8 | Di-tert-butyl (1S,2R,3S,4S,5R,6R)-2-(tert-butoxycarbonylamino)-3-[(4-fluorophenyl)sulfanylmethyl]-4-hydroxy-bicyclo[3.1.0]hexane-2,6-dicarboxylate | 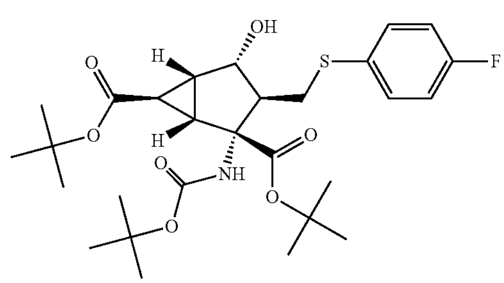 [SMILES: CC(C)(C)OC(=O)N[C@]1(C(=O)OC(C)(C)C)[C@@H]2[C@@H](C(=O)OC(C)(C)C)[C@@H]2[C@H](O)[C@H]1CSc1ccc(F)cc1] | 50.3 | (M + Na): 576.0 |

| Prep. No. | Chemical Name | Structure | Yield (%) | Physical Data MS(m/z) |
|---|---|---|---|---|
| 9 | Di-tert-butyl (1S,2R,3S,4S,5R,6R)-2-(tert-butoxycarbonylamino)-4-hydroxy-3-(p-tolylsulfanylmethyl)bicyclo[3.1.0]hexane-2,6-dicarboxylate | 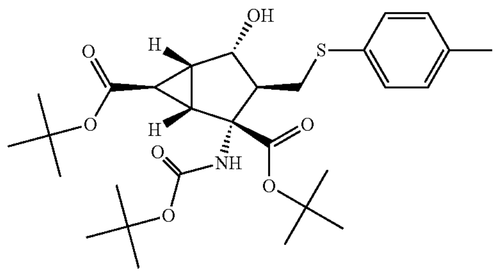 [SMILES: Cc1ccc(SC[C@@H]2[C@@H](O)[C@H]3[C@H](C(=O)OC(C)(C)C)[C@H]3[C@]2(NC(=O)OC(C)(C)C)C(=O)OC(C)(C)C)cc1] | 77.0 | (M + Na): 572.2 |

Preparation 10: Di-tert-butyl (1S,2R,3S,4R,5R,6R)-2-[(tert-butoxycarbonyl)amino]-3-{[(4-fluoro-3-methyl-phenyl)sulfanyl]methyl}-4-hydroxybicyclo[3.1.0]hexane-2,6-dicarboxylate

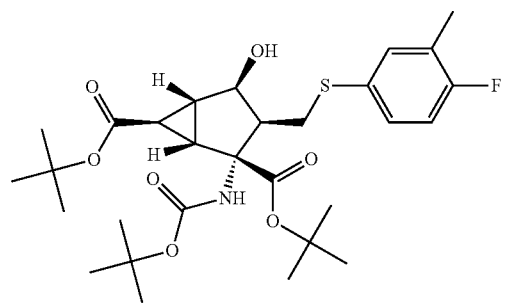 [SMILES: Cc1cc(SC[C@@H]2[C@H](O)[C@H]3[C@H](C(=O)OC(C)(C)C)[C@H]3[C@]2(NC(=O)OC(C)(C)C)C(=O)OC(C)(C)C)ccc1F]

Di-tert-butyl (1S,2R,5R,6R)-2-(tert-butoxycarbonylamino)-3-methylene-4-oxo-bicyclo[3.1.0]hexane-2,6-dicarboxylate (8 g, 18.9 mmol) in diethyl ether (80 mL) is bubbled with nitrogen gas for 10 minutes. 4-fluoro-3-methyl-benzenethiol (2.7 g, 18.9 mmol) and triethylamine (0.26 mL, 1.89 mmol) are added. The mixture is warmed to 40° C. and stirred for 15 minutes. The mixture is then allowed to cool to ambient temperature, transferred to addition funnel and added slowly over 2 hours to a 200 ml ether solution at −10° C. which contains S-(−)-2-methyl-CBS-oxazaborolidine (1M in tetrahydrofuran) (5.67 mL, 5.67 mmol) and borane-methyl sulfide complex (2M in tetrahydrofuran, 8.5 mL, 17 mmol). The mixture is stirred for an additional hour after final addition. Silica gel (40 g) is added over 30 minutes and the reaction mixture is gradually warmed to ambient temperature. The suspension is filtered, and washed with 300 ml of diethyl ether. The solvent is concentrated under reduced pressure giving a residue. The residue is purified by flash chromatography, eluting with (0 to 25% ethyl acetate/hexanes) to give the title compound (9.8 g, 17.3 mmol, 91.5% yield). MS (m/z): 565.8 (M−H).

Preparation 11: Di-tert-butyl (1S,2R,3S,4R,5R,6R)-2-(tert-butoxycarbonylamino)-3-[(4-fluoro-3-methylphenyl)sulfanylmethyl]-4-methylsulfonyloxy-bicyclo[3.1.0]hexane-2,6-dicarboxylate

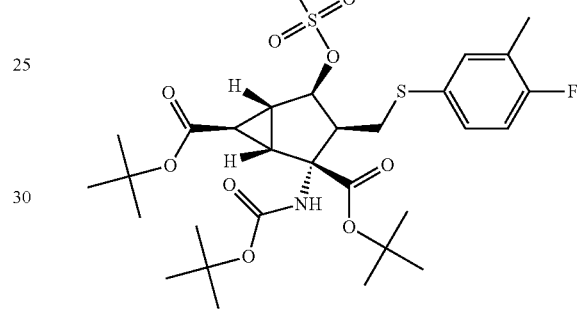

Di-tert-butyl (1S,2R,3S,4R,5R,6R)-2-(tert-butoxycarbonylamino)-3-[(4-fluoro-3-methyl-phenyl)sulfanylmethyl]-4-hydroxy-bicyclo[3.1.0]hexane-2,6-dicarboxylate (4.6 g, 8.10 mmol) in pyridine (60 mL) is cooled to 0° C. To this mixture is added methanesulfonyl chloride (1.88 ml, 24.31 mmol). The mixture is warmed to 40° C. and stirred for 1 hour, and cooled to ambient temperature and allowed to stir for 18 hours. The mixture is concentrated under reduced pressure to give a residue. The residue is partitioned between ethyl acetate and 1N aqueous HCl (2×50 mL). The organic layer is separated, dried over magnesium sulfate, filtered, and concentrated under reduced pressure to give the title compound (5.2 g, 8.05 mmol, 99.4% yield): MS (m/z): 643.6 (M−H).

Preparation 12: Di-tert-butyl (1R,2R,3R,4S,5R,6R)-2-(tert-butoxycarbonylamino)-3-[(4-fluoro-3-methylphenyl)sulfanylmethyl]-4-(1H-1,2,4-triazol-3-ylsulfanyl)bicyclo[3.1.0]hexane-2,6-dicarboxylate

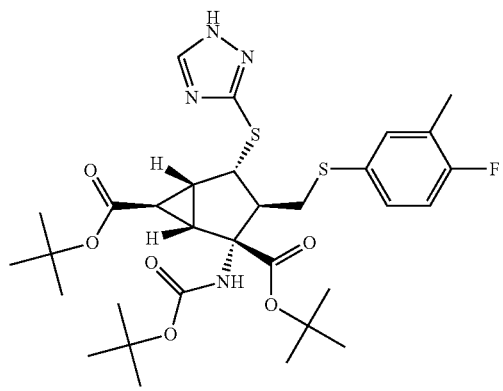 [SMILES: Cc1cc(SC[C@@H]2[C@@H](Sc3nc[nH]n3)[C@H]3[C@H](C(=O)OC(C)(C)C)[C@H]3[C@]2(NC(=O)OC(C)(C)C)C(=O)OC(C)(C)C)ccc1F]

Di-tert-butyl (1S,2R,3S,4R,5R,6R)-2-(tert-butoxycarbonylamino)-3-[(4-fluoro-3-methyl-phenyl)sulfanylmethyl]-4-methylsulfonyloxy-bicyclo[3.1.0]hexane-2,6-dicarboxylate (5.3 g, 8.21 mmol) is dissolved in dimethylformamide (100 mL). To this mixture is added cesium carbonate (5.40 g, 16.41 mmol), 1H-1,2,4-triazole-3-thiol (3.42 g, 32.83 mmol), and sodium triacetoxyborohydride (906 mg, 4.10 mmol). The mixture is stirred at 40° C. for 72 hours. The reaction is cooled and quenched with water and aqueous NH$_4$Cl. The mixture is transferred to a separatory funnel and extracted with diethyl ether, dried over magnesium sulfate, filtered, and concentrated under reduced pressure to give a residue. The residue is purified by flash chromatography (0 to 50% ethyl acetate/hexanes) to give the title compound (0.88 g, 1.35 mmol, 16.5% yield). MS (m/z): 651 (M+H).

Preparation 13: Di-tert-butyl (1S,2R,3R,4S,5R,6S)-4-azido-2-(tert-butoxycarbonylamino)-3-[4-fluoro-3-methyl-phenyl)sulfanylmethyl]bicyclo[3.1.0]hexane-2,6-dicarboxylate

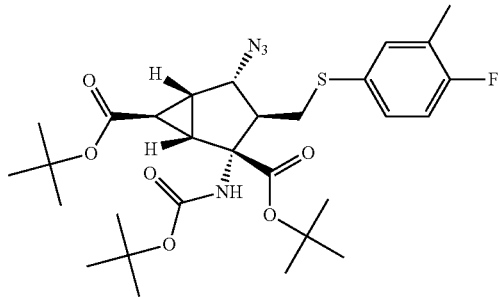 [SMILES: Cc1cc(SC[C@@H]2[C@@H](N=[N+]=[N-])[C@H]3[C@H](C(=O)OC(C)(C)C)[C@H]3[C@]2(NC(=O)OC(C)(C)C)C(=O)OC(C)(C)C)ccc1F]

Di-tert-butyl (1S,2R,3S,4R,5R,6R)-2-(tert-butoxycarbonylamino)-3-[(4-fluoro-3-methyl-phenyl)sulfanylmethyl]-4-methylsulfonyloxy-bicyclo[3.1.0]hexane-2,6-dicarboxylate (5.9 g, 9.14 mmol) is dissolved in dimethyl sulfoxide (30 mL). To this mixture is added sodium azide (2.5 g, 38.37 mmol). The mixture is stirred at 100° C. for 18 hours. The solvent was removed under reduced pressure to give a residue. The residue is suspended in diethyl ether (100 ml) and filtered. The organic layer is transferred to a separatory funnel and washed with water and brine, dried over magnesium sulfate, filtered, and concentrated under reduced pressure to give a residue. The residue is purified by flash chromatography (0 to 15% ethyl acetate/hexanes) to give the title compound (3.14 g, 5.30 mmol, 58% yield). MS (m/z): 591 (M–H).

Preparation 14: Di-tert-butyl (1S,2R,3R,4S,5R,6S)-4-amino-2-(tert-butoxycarbonylamino)-3-[4-fluoro-3-methyl-phenyl)sulfanylmethyl]bicyclo[3.1.0]hexane-2,6-dicarboxylate

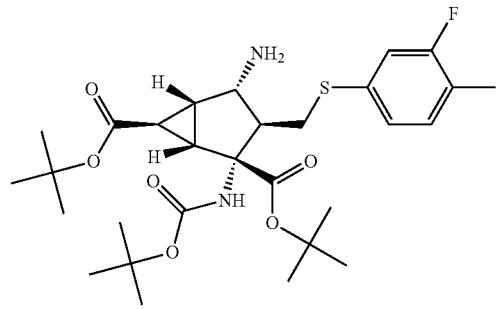 [SMILES: Cc1ccc(SC[C@@H]2[C@@H](N)[C@H]3[C@H](C(=O)OC(C)(C)C)[C@H]3[C@]2(NC(=O)OC(C)(C)C)C(=O)OC(C)(C)C)cc1F]

Di-tert-butyl (1S,2R,3R,4S,5R,6S)-4-azido-2-(tert-butoxycarbonylamino)-3-[(4-fluoro-3-methyl-phenyl)sulfanylmethyl]bicyclo[3.1.0]hexane-2,6-dicarboxylate (1.88 g, 3.17 mmol) is dissolved in methanol (15.86 mL). To this mixture is added triethylamine (1.77 mL, 12.7 mmol) and 1,3-propanedithiol (1.28 mL, 12.69 mmol). The mixture is stirred at ambient temperature for 18 hours. The mixture is poured into water and extracted with ethyl acetate, dried over sodium sulfate, filtered, and concentrated under reduced pressure to give a residue. The residue is purified by flash chromatography (50 to 100% ethyl acetate/hexanes) to give the title compound (1.2 g, 2.12 mmol, 66.76% yield). MS (m/z): 567.2 (M+1).

Preparation 15: Di-tert-butyl (1S,2R,3R,4S,5R,6S)-4-acetamido-2-(tert-butoxycarbonylamino)-3-[(4-fluoro-3-methyl-phenyl)sulfanylmethyl]bicyclo[3.1.0]hexane-2,6-dicarboxylate

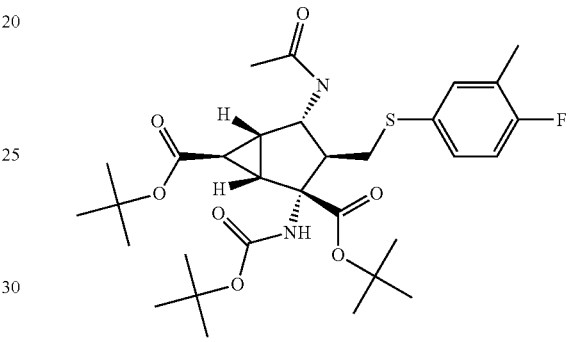

Di-tert-butyl (1S,2R,3R,4S,5R,6S)-4-amino-2-(tert-butoxycarbonylamino)-3-[(4-fluoro-3-methyl-phenyl)sulfanylmethyl]bicyclo[3.1.0]hexane-2,6-dicarboxylate (0.15 g, 264.67 μmol) is dissolved in dichloromethane (10 mL). To this mixture is added triethylamine (55.34 μL, 397.01 μmol) and acetyl chloride (28.25 μL, 397.01 μmol). The mixture is stirred at ambient temperature for 10 minutes. The solvent is removed under reduced pressure to give a residue. The residue is purified by flash chromatography (10% to 100% ethyl acetate/hexanes) to give the title compound (100 mg, 164.27 μmol, 62.06% yield); $^1$H NMR (CD3Cl) δ 1.44 (t, 27H), 1.95 (s, 3H), 2.16 (m, 1H), 2.22 (s, 3H), 2.60 (dd, 1H), 2.78 (bs, 1H), 3.10 (dd, 1H), 4.59 (m, 1H), 5.50 (d, 1H), 6.92 (t, 1H), 7.06 (m, 1H), 7.11 (d, 1H).

Preparation 16: (1S,2R,3S,4S,5R,6R)-2-[(tert-butoxycarbonyl)amino]-3-{[(3,4-difluorophenyl)sulfanyl]methyl}-4-hydroxybicyclo[3.1.0]hexane-2,6-dicarboxylic acid

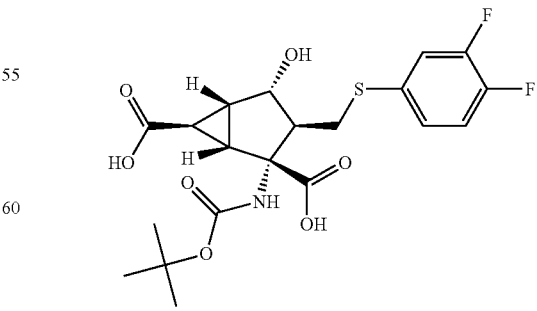

Di-tert-butyl (1S,2R,3S,4S,5R,6R)-2-[(tert-butoxycarbonyl)amino]-3-{[(3,4-difluorophenyl)sulfanyl]methyl}-4-hydroxybicyclo[3.1.0]hexane-2,6-dicarboxylate (4.11 g, 7.19 mmol) is weighed into a one liter round bottom with a stirring bar. Hydrogen chloride (4N in dioxane, 120 mL, 480.0 mmol) is added. The mixture is warmed to 70° C. for 2 hours and then allowed to cool to ambient temperature. The solvent is removed under reduced pressure to give a residue. The residue is dissolve in dichloromethane (200 mL) and the solvent is removed under reduced pressure to give a residue. This is repeated two more times to give (1S,2R,3S,4S,5R,6R)-2-amino-3-[(3,4-difluorophenyl)sulfanylmethyl]-4-hydroxy-bicyclo[3.1.0]hexane-2,6-dicarboxylic acid hydrochloride. This material is taken up in tetrahydrofuran (100 mL) as a suspension. To this suspension is added triethylamine (40.08 mL, 287.57 mmol). The suspension is stirred for 10 minutes and then methanol (50 ml) is added. To the reaction is added di-t-butyldicarbonate (4.71 g, 21.57 mmol) and the mixture is heated to 80° C. for 2 hours. The mixture is allowed to come to ambient temperature and the solvent is removed under reduced pressure to give a residue. The residue is dissolved in acetonitrile (50 ml), transferred to a separatory funnel and washed with hexanes. The acetonitrile layer is separated and removed under reduced pressure to give a residue. The residue is suspended in diethyl ether, transferred to a separatory funnel, washed with 1 N aqueous HCl, dried over magnesium sulfate, filtered, and concentrated under reduced pressure giving the title compound (3 g, 6.53 mmol, 90.82% yield). MS (m/z): 457.8 (M−H).

The following compounds are prepared essentially by the method of Preparation 16:

| Prep. No. | Chemical Name | Structure | Yield (%) | Physical Data MS(m/z) |
|---|---|---|---|---|
| 17 | (1S,2R,3S,4S,5R,6R)-2-(tert-Butoxycarbonylamino)-3-[(3-chloro-4-fluoro-phenyl)sulfanylmethyl]-4-hydroxy-bicyclo[3.1.0]hexane-2,6-dicarboxylic acid | 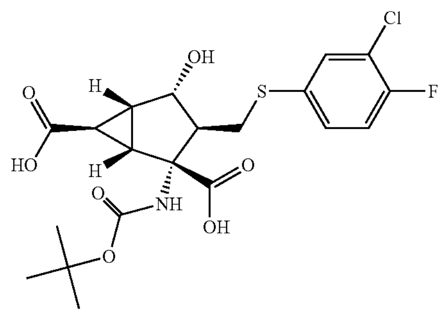 [SMILES: CC(C)(C)OC(=O)N[C@]1(C(=O)O)[C@@H]2[C@@H](C(=O)O)[C@@H]2[C@H](O)[C@H]1CSc1ccc(F)c(Cl)c1] | 76.2 | (M + H): 476.0 |
| 18 | (1S,2R,3S,4S,5R,6R)-2-(tert-Butoxycarbonylamino)-3-[(4-fluoro-3-methyl-phenyl)sulfanylmethyl]-4-hydroxy-bicyclo[3.1.0]hexane-2,6-dicarboxylic acid | 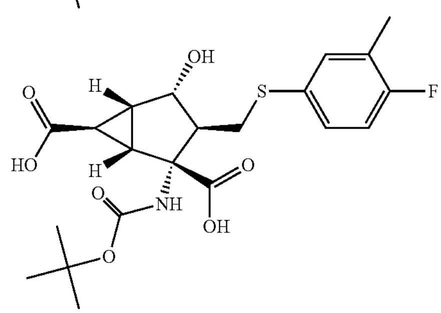 | 94.6 | (M − H): 453.8 |
| 19 | (1S,2R,3S,4S,5R,6R)-2-(tert-Butoxycarbonylamino)-3-[(3,4-dimethylphenyl)sulfanylmethyl]-4-hydroxy-bicyclo[3.1.0]hexane-2,6-dicarboxylic acid | 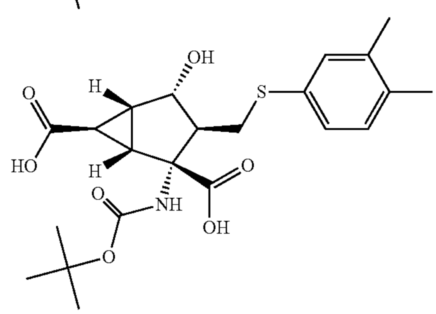 | 92.3 | (M + H): 450.2 |
| 20 | Di-tert-butyl (1S,2R,3S,4S,5R,6R)-2-(tert-butoxycarbonylamino)-3-[(3-chlorophenyl)sulfanylmethyl]-4-hydroxy-bicyclo[3.1.0]hexane-2,6-dicarboxylate | 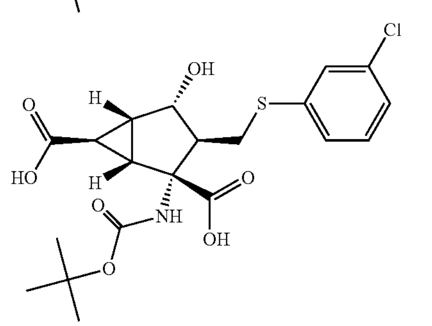 | 95.6 | (M − H): 440.0 |

Preparation 21: Bis(chloromethyl)(1S,2R,3S,4S,5R,6R)-2-(tert-butoxycarbonylamino)-3-[(4-fluoro-3-methyl-phenyl)sulfanylmethyl]-4-hydroxy-bicyclo[3.1.0]hexane-2,6-dicarboxylate

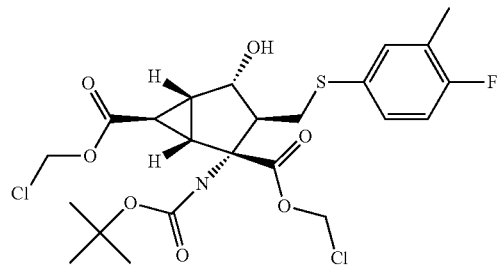 [SMILES: Cc1cc(SC[C@@H]2[C@@H](O)[C@H]3[C@H](C(=O)OCCl)[C@H]3[C@]2(NC(=O)OC(C)(C)C)C(=O)OCCl)ccc1F]

To a stirring mixture of (1S,2R,3S,4S,5R,6R)-2-(tert-butoxycarbonylamino)-3-[(4-fluoro-3-methyl-phenyl)sulfanylmethyl]-4-hydroxy-bicyclo[3.1.0]hexane-2,6-dicarboxylic acid (2.4 g, 5.27 mmol), tetra(n-butyl)ammonium bisulfate (178.90 mg, 526.89 μmoles), and sodium bicarbonate (3.54 g, 42.15 mmol) in dichloromethane (13.2 mL) and water (13.2 mL) is added chloromethyl chlorosulfate (1.20 mL, 11.59 mmol). The mixture is stirred at ambient temperature for 18 hours. The reaction is poured over water and extracted with dichloromethane. The combined organics are dried over magnesium sulfate, filtered and concentrated to give a residue. The residue is purified by flash chromatography (20-35% ethyl acetate/hexane) to give the title compound (1.37 g, 2.48 mmol, 47% yield). MS (m/z): 574.0 (M+Na).

The following compound is prepared essentially by the method of Preparation 21:

Preparation 24: Bis({[(1-methylethoxy)carbonyl]oxy}methyl)(1S,2R,3S,4S,5R,6R)-2-[(tert-butoxycarbonyl)amino]-3-{[(3,4-difluorophenyl)sulfanyl]methyl}-4-hydroxybicyclo[3.1.0]hexane-2,6-dicarboxylate

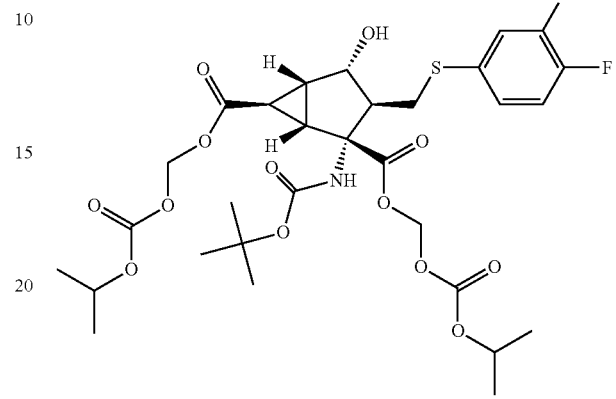

Add potassium carbonate (668.43 mg, 4.79 mmol), sodium iodide (75.03 mg, 500.58 mmol) to (1S,2R,3S,4S,5R,6R)-2-(tert-butoxycarbonylamino)-3-[(3,4-difluorophenyl)sulfanylmethyl]-4-hydroxybicyclo[3.1.0]hexane-2,6-dicarboxylic acid (1 g, 2.18 mmol) in dimethylformamide (13.06 mL). The mixture is stirred for 10 minutes at ambient temperature. Chloromethyl isopropyl carbonate (1 g, 6.53 mmol) is added. The mixture is stirred at ambient temperature for 18 hours. Acetic acid (4 ml) is added and the mixture is stirred for 10 minutes. The solvent volume is reduced by about 10 ml under reduced pressure to give a viscous residue. The residue is

| Prep. No. | Chemical Name | Structure | Yield (%) | Physical Data MS(m/z) or NMR |
|---|---|---|---|---|
| 22 | (Bis(chloromethyl) (1S,2R,3S,4S,5R,6R)-2-(tert-butoxycarbonylamino)-3-[(3-chloro-4-fluoro-phenyl)sulfanylmethyl]-4-hydroxy-bicyclo[3.1.0]hexane-2,6-dicarboxylate | 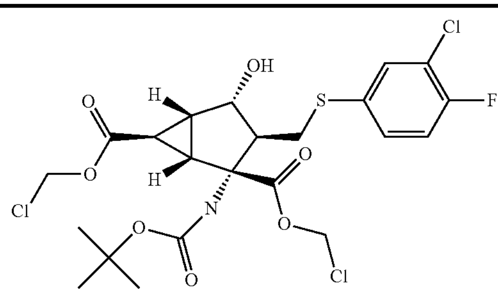 | 31.2 | (M + Na): 593.97 |
| 23 | Chloromethyl 2-methylpropanoate | | 95.8 | $^1$H NMR (CD3Cl) δ 1.17 (d, 6H), 2.58 (m, 1H), 2.48 (d, 1H), 5.67 (s, 2H) | diluted with diethyl ether and stirred for 10 minutes. The solution is passed through a filter and the solvent is removed under reduced pressure to give a residue. The residue is left under high vacuum for 1 hour. The residue is purified by flash chromatography, eluted with (0 to 35% tetrahydrofuran/hexanes) to give the title compound (0.88 g, 1.27 mmol, 58.5% yield). MS (m/z): 714.2 (M+Na).

The following compounds are prepared essentially by the method of Preparation 24:

| Prep. No. | Chemical Name | Structure | Yield (%) | Physical Data MS(m/z) |
|---|---|---|---|---|
| 25 | (Bis(isopropoxycarbonyloxymethyl) (1S,2R,3S,4S,5R,6R)-2-(tert-butoxycarbonylamino)-3-[(3-chloro-4-fluoro-phenyl)sulfanylmethyl]-4-hydroxy-bicyclo[3.1.0]hexane-2,6-dicarboxylate | 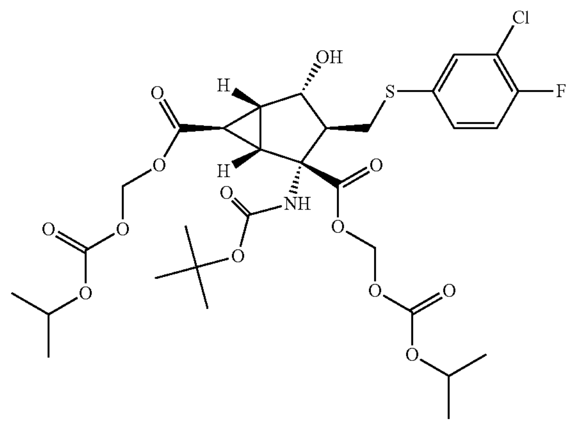 [SMILES: CC(C)OC(=O)OCOC(=O)[C@H]1[C@@H]2[C@H](O)[C@@H](CSc3ccc(F)c(F)c3)[C@@](NC(=O)OC(C)(C)C)(C(=O)OCOC(=O)OC(C)C)[C@H]12] | 52.9 | (M + Na): 730.2 |
| 26 | Bis(isopropoxycarbonyloxymethyl) (1S,2R,3S,4S,5R,6R)-2-(tert-butoxycarbonylamino)-3-[(4-fluoro-3-methyl-phenyl)sulfanylmethyl]-4-hydroxy-bicyclo[3.1.0]hexane-2,6-dicarboxylate | 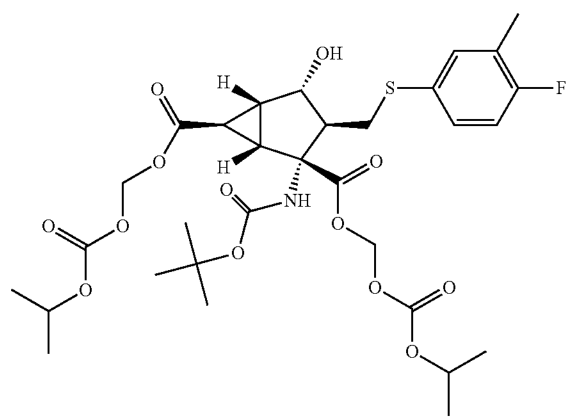 | 35.8 | (M + Na): 709.8 |
| 27 | Bis(ethoxycarbonyloxymethyl) (1S,2R,3S,4S,5R,6R)-2-(tert-butoxycarbonylamino)-3-[(3,4-difluorophenyl)sulfanylmethyl]-4-hydroxy-bicyclo[3.1.0]hexane-2,6-dicarboxylate | 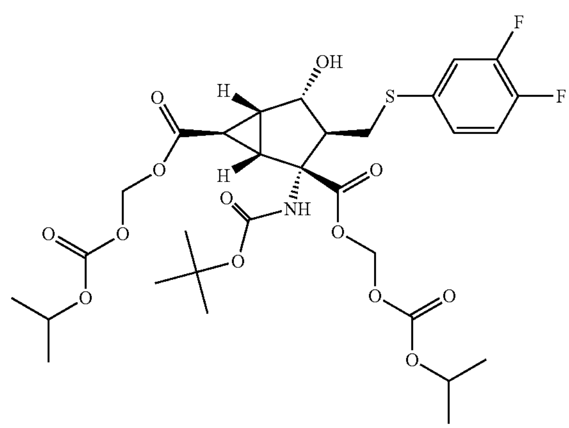 [SMILES: CC(C)OC(=O)OCOC(=O)[C@H]1[C@@H]2[C@H](O)[C@@H](CSc3ccc(F)c(F)c3)[C@@](NC(=O)OC(C)(C)C)(C(=O)OCOC(=O)OC(C)C)[C@H]12] | 62.7 | (M + Na): 686.2 |

-continued

| Prep. No. | Chemical Name | Structure | Yield (%) | Physical Data MS(m/z) |
|---|---|---|---|---|
| 28 | Bis(ethoxycarbonyloxymethyl) (1S,2R,3S,4S,5R,6R)-2-(tert-butoxycarbonylamino)-3-[(3-chloro-4-fluoro-phenyl)sulfanylmethyl]-4-hydroxy-bicyclo[3.1.0]hexane-2,6-dicarboxylate | 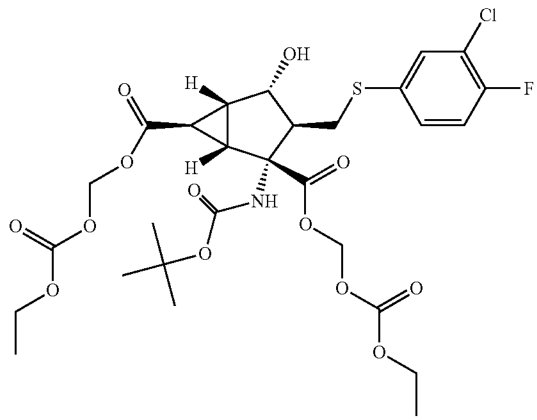 [SMILES: CCOC(=O)OCOC(=O)[C@H]1[C@@H]2[C@H](O)[C@@H](CSc3ccc(F)c(Cl)c3)[C@@](NC(=O)OC(C)(C)C)(C(=O)OCOC(=O)OCC)[C@H]12] | 44.9 | (M + Na): 702.2 |
| 29 | Bis(ethoxycarbonyloxymethyl) (1S,2R,3S,4S,5R,6R)-2-(tert-butoxycarbonylamino)-3-[(4-fluoro-3-methyl-phenyl)sulfanylmethyl]-4-hydroxy-bicyclo[3.1.0]hexane-2,6-dicarboxylate | 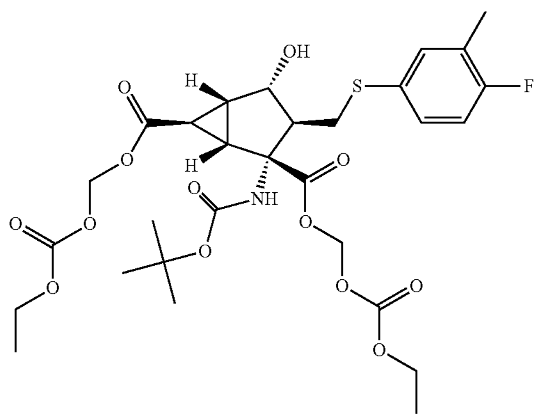 [SMILES: CCOC(=O)OCOC(=O)[C@H]1[C@@H]2[C@H](O)[C@@H](CSc3ccc(F)c(C)c3)[C@@](NC(=O)OC(C)(C)C)(C(=O)OCOC(=O)OCC)[C@H]12] | 39.7 | (M + Na): 682.0 |
| 30 | Bis(ethoxycarbonyloxymethyl) (1S,2R,3S,4S,5R,6R)-2-(tert-butoxycarbonylamino)-3-[(3,4-dimethylphenyl)sulfanylmethyl]-4-hydroxy-bicyclo[3.1.0]hexane-2,6-dicarboxylate | 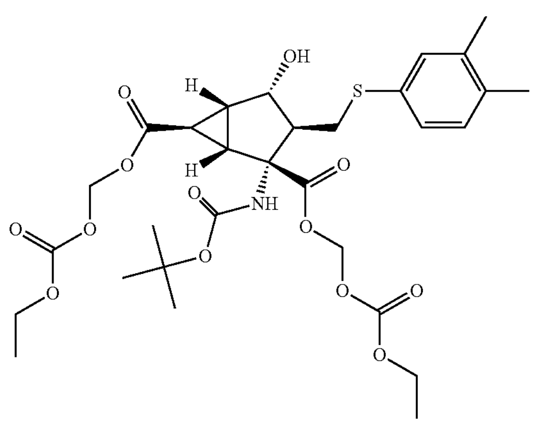 [SMILES: CCOC(=O)OCOC(=O)[C@H]1[C@@H]2[C@H](O)[C@@H](CSc3ccc(C)c(C)c3)[C@@](NC(=O)OC(C)(C)C)(C(=O)OCOC(=O)OCC)[C@H]12] | 31.4 | (M + Na): 677.8 |

-continued

| Prep. No. | Chemical Name | Structure | Yield (%) | Physical Data MS(m/z) |
|---|---|---|---|---|
| 31 | Bis(ethoxycarbonyloxymethyl) (1S,2R,3S,4S,5R,6R)-2-(tert-butoxycarbonylamino)-3-[(4-fluorophenyl)sulfanylmethyl]-4-hydroxy-bicyclo[3.1.0]hexane-2,6-dicarboxylate | 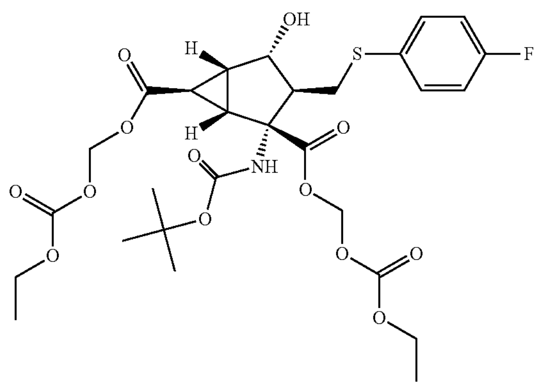 [SMILES: CCOC(=O)OCOC(=O)[C@H]1[C@@H]2[C@H](O)[C@@H](CSc3ccc(F)cc3)[C@@](NC(=O)OC(C)(C)C)(C(=O)OCOC(=O)OCC)[C@H]12] | 62.4 | (M + Na): 668.2 |
| 32 | Bis(acetoxymethyl) (1S,2R,3S,4S,5R,6R)-2-(tert-butoxycarbonylamino)-3-[(4-fluoro-3-methyl-phenyl)sulfanylmethyl]-4-hydroxy-bicyclo[3.1.0]hexane-2,6-dicarboxylate | 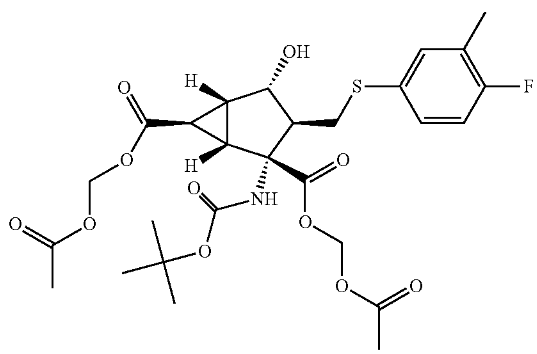 [SMILES: CC(=O)OCOC(=O)[C@H]1[C@@H]2[C@H](O)[C@@H](CSc3ccc(F)c(C)c3)[C@@](NC(=O)OC(C)(C)C)(C(=O)OCOC(C)=O)[C@H]12] | 60.3 | (M + Na): 622.00 |
| 33 | Bis(acetoxymethyl) (1S,2R,3S,4S,5R,6R)-2-(tert-butoxycarbonylamino)-3-[(3-chloro-4-fluoro-phenyl)sulfanylmethyl]-4-hydroxy-bicyclo[3.1.0]hexane-2,6-dicarboxylate | 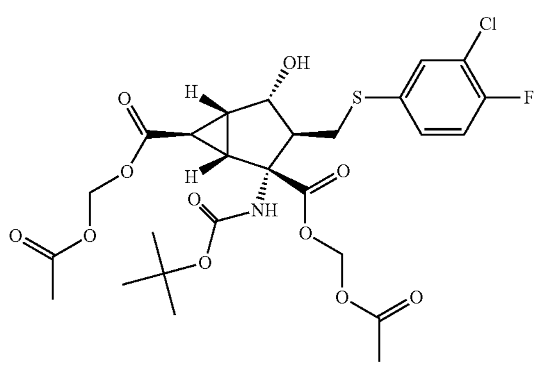 [SMILES: CC(=O)OCOC(=O)[C@H]1[C@@H]2[C@H](O)[C@@H](CSc3ccc(F)c(Cl)c3)[C@@](NC(=O)OC(C)(C)C)(C(=O)OCOC(C)=O)[C@H]12] | 51.2 | (M + Na): 642.00 |
| 34 | Bis(2-methylpropanoyloxymethyl) (1S,2R,3S,4S,5R,6R)-2-(tert-butoxycarbonylamino)-3-[(3,4-difluorophenyl)sulfanylmethyl]-4-hydroxy-bicyclo[3.1.0]hexane-2,6-dicarboxylate | 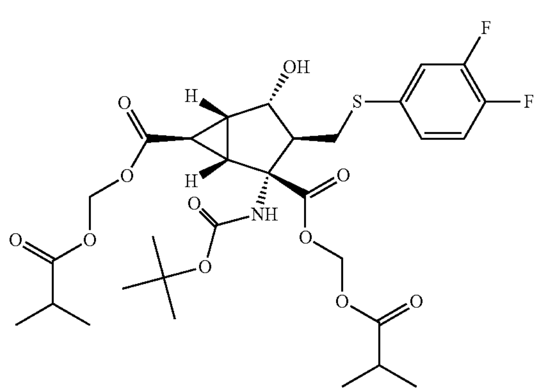 | 29.5 | (M + Na): 682.00 |

Preparation 35: Bis {[(2-methylpropanoyl)oxy]methyl}(1S,2R,3S,4S,5R,6R)-2-[(tert-butoxycarbonyl)amino]-3-{[(4-fluoro-3-methylphenyl)sulfanyl]methyl}-4-hydroxybicyclo[3.1.0]hexane-2,6-dicarboxylate

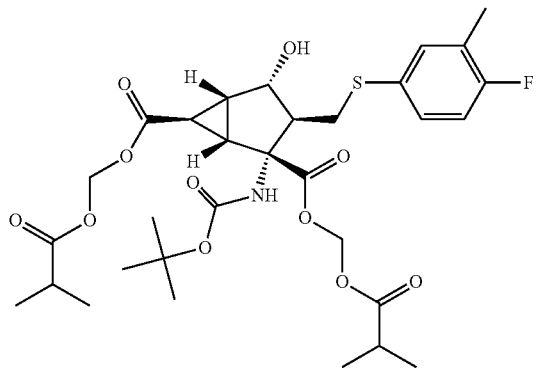 [SMILES: Cc1cc(SC[C@@H]2[C@@H](O)[C@H]3[C@H](C(=O)OCOC(=O)C(C)C)[C@H]3[C@]2(NC(=O)OC(C)(C)C)C(=O)OCOC(=O)C(C)C)ccc1F]

Isobutyric acid (0.21 g, 2.42 mmol) is dissolved in dimethylformamide (10 mL). To this solution is added the potassium carbonate (0.54 g, 3.87 mmol). The mixture is stirred at 50° C. for 3 hours and then cooled to room temperature. To the mixture is added bis(chloromethyl)(1S,2R,3S,4S,5R,6R)-2-(tert-butoxycarbonylamino)-3-[(4-fluoro-3-methyl-phenyl)sulfanylmethyl]-4-hydroxy-bicyclo[3.1.0]hexane-2,6-dicarboxylate (535 mg, 0.97 mmol). The mixture is stirred at ambient temperature for 18 hours. The mixture is diluted with ethyl acetate, transferred to a separatory funnel, washed with brine, dried over magnesium sulfate, and concentrated under reduced pressure to give a residue. The residue is purified by flash chromatography (10-40% ethyl acetate/hexanes) to give the title compound (230 mg, 0.36 mmol, 37%). MS (m/z): 678.2 (M+Na).

The following compounds are prepared essentially by the method of Preparation 35:

| Prep. No. | Chemical Name | Structure | Yield (%) | Physical Data MS(m/z) |
|---|---|---|---|---|
| 36 | (Bis(2-methylpropanoyloxymethyl)(1S,2R,3S,4S,5R,6R)-2-(tert-butoxycarbonylamino)-3-[(3-chloro-4-fluoro-phenyl)sulfanylmethyl]-4-hydroxy-bicyclo[3.1.0]hexane-2,6-dicarboxylate | 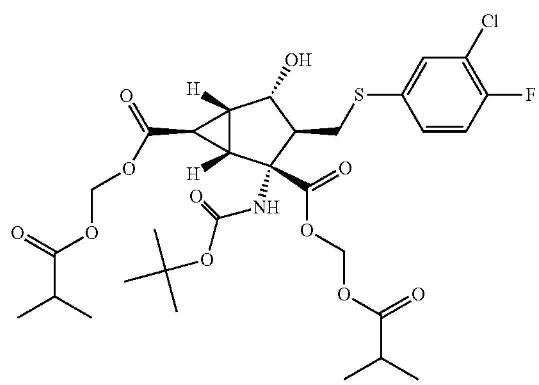 [SMILES: CC(C)C(=O)OCOC(=O)[C@H]1[C@@H]2[C@H](O)[C@@H](CSc3ccc(F)c(Cl)c3)[C@@](NC(=O)OC(C)(C)C)(C(=O)OCOC(=O)C(C)C)[C@H]12] | 37.0 | (M + Na): 698.0 |
| 37 | Bis[[(2S)-2-methylbutanoyl]oxymethyl](1S,2R,3S,4S,5R,6R)-2-(tert-butoxycarbonylamino)-3-[(4-fluoro-3-methyl-phenyl)sulfanylmethyl]-4-hydroxy-bicyclo[3.1.0]hexane-2,6-dicarboxylate | 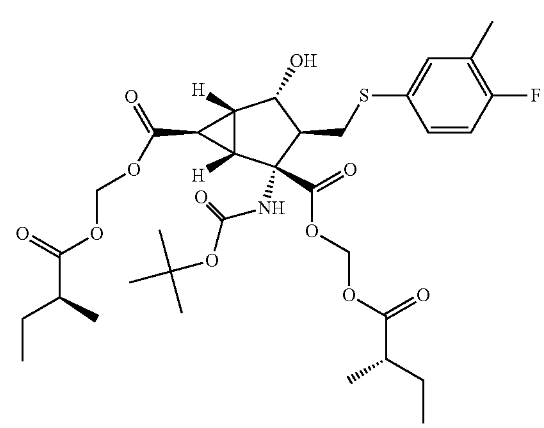 [SMILES: CC[C@H](C)C(=O)OCOC(=O)[C@H]1[C@@H]2[C@H](O)[C@@H](CSc3ccc(F)c(C)c3)[C@@](NC(=O)OC(C)(C)C)(C(=O)OCOC(=O)[C@@H](C)CC)[C@H]12] | 52.0 | (M + Na): 706.2 |

-continued

| Prep. No. | Chemical Name | Structure | Yield (%) | Physical Data MS(m/z) |
|---|---|---|---|---|
| 38 | Bis(2-ethylbutanoyloxymethyl) (1S,2R,3S,4S,5R,6R)-2-(tert-butoxycarbonylamino)-3-[(4-fluoro-3-methyl-phenyl)sulfanylmethyl]-4-hydroxy-bicyclo[3.1.0]hexane-2,6-dicarboxylate | 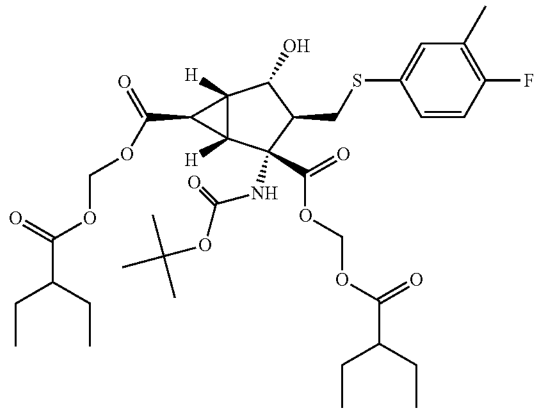 [SMILES: CCC(CC)C(=O)OCOC(=O)[C@H]1[C@@H]2[C@H](O)[C@@H](CSc3ccc(F)c(C)c3)[C@@](NC(=O)OC(C)(C)C)(C(=O)OCOC(=O)C(CC)CC)[C@H]12] | 30.2 | (M + Na): 733.8 |
| 39 | Bis(3-methylbutanoyloxymethyl) (1S,2R,3S,4S,5R,6R)-2-(tert-butoxycarbonylamino)-3-[(4-fluoro-3-methyl-phenyl)sulfanylmethyl]-4-hydroxy-bicyclo[3.1.0]hexane-2,6-dicarboxylate | 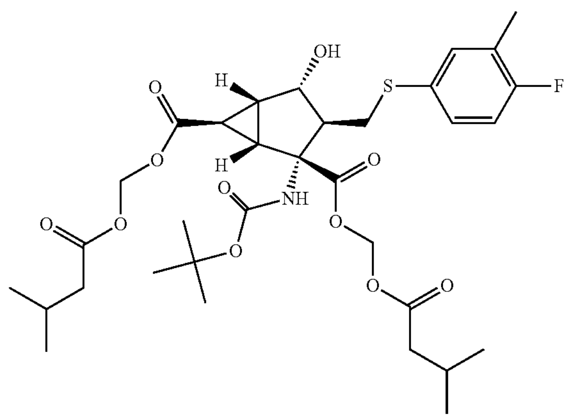 [SMILES: Cc1cc(SC[C@@H]2[C@@H](O)[C@H]3[C@H](C(=O)OCOC(=O)CC(C)C)[C@H]3[C@]2(NC(=O)OC(C)(C)C)C(=O)OCOC(=O)CC(C)C)ccc1F] | 29.1 | (M + Na): 706.2 |
| 40 | Bis(cyclopropanecarbonyloxymethyl) (1S,2R,3S,4S,5R,6R)-2-(tert-butoxycarbonylamino)-3-[(4-fluoro-3-methyl-phenyl)sulfanylmethyl]-4-hydroxy-bicyclo[3.1.0]hexane-2,6-dicarboxylate | 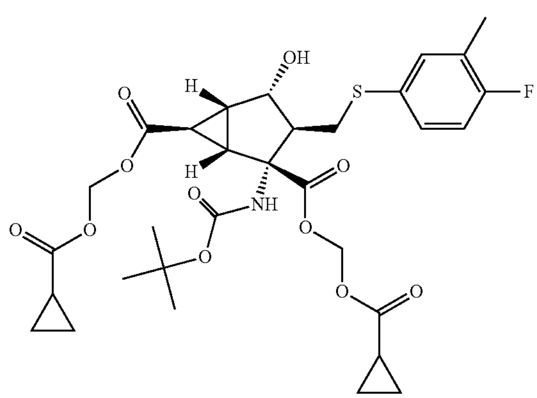 [SMILES: Cc1cc(SC[C@@H]2[C@@H](O)[C@H]3[C@H](C(=O)OCOC(=O)C4CC4)[C@H]3[C@]2(NC(=O)OC(C)(C)C)C(=O)OCOC(=O)C2CC2)ccc1F] | 40.6 | (M + Na): 674.0 |

-continued

| Prep. No. | Chemical Name | Structure | Yield (%) | Physical Data MS(m/z) |
|---|---|---|---|---|
| 41 | Bis(cyclopentanecarbonyloxymethyl) (1S,2R,3S,4S,5R,6R)-2-(tert-butoxycarbonylamino)-3-[(4-fluoro-3-methyl-phenyl)sulfanylmethyl]-4-hydroxy-bicyclo[3.1.0]hexane-2,6-dicarboxylate | 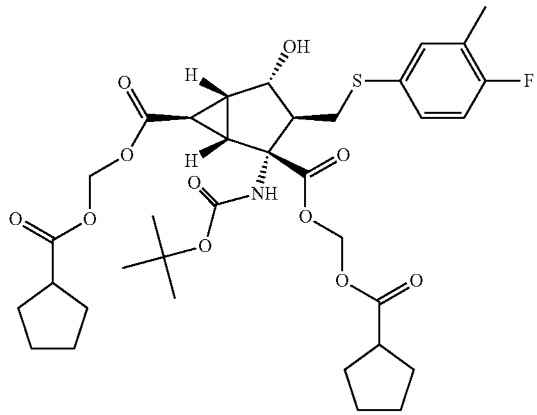 [SMILES: Cc1cc(SC[C@@H]2[C@@H](O)[C@H]3[C@H](C(=O)OCOC(=O)C4CCCC4)[C@H]3[C@]2(NC(=O)OC(C)(C)C)C(=O)OCOC(=O)C2CCCC2)ccc1F] | 51.8 | (M + Na): 730.2 |
| 42 | Bis(propanoyloxymethyl) (1S,2R,3S,4S,5R,6R)-2-(tert-butoxycarbonylamino)-3-[(4-fluoro-3-methyl-phenyl)sulfanylmethyl]-4-hydroxy-bicyclo[3.1.0]hexane-2,6-dicarboxylate | 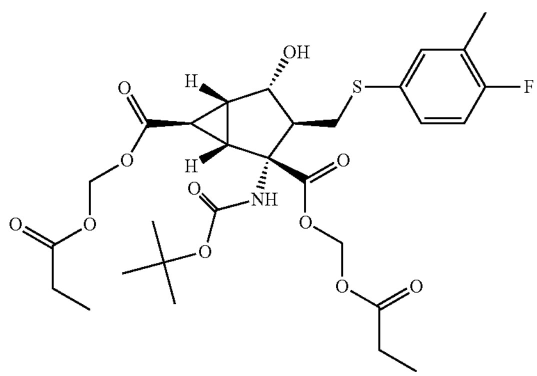 [SMILES: CCC(=O)OCOC(=O)[C@H]1[C@@H]2[C@H](O)[C@@H](CSc3ccc(F)c(C)c3)[C@@](NC(=O)OC(C)(C)C)(C(=O)OCOC(=O)CC)[C@H]12] | 19.8 | (M + Na): 650.0 |
| 43 | Bis(propanoyloxymethyl) (1S,2R,3S,4S,5R,6R)-2-(tert-butoxycarbonylamino)-3-[(3-chloro-4-fluoro-phenyl)sulfanylmethyl]-4-hydroxy-bicyclo[3.1.0]hexane-2,6-dicarboxylate | 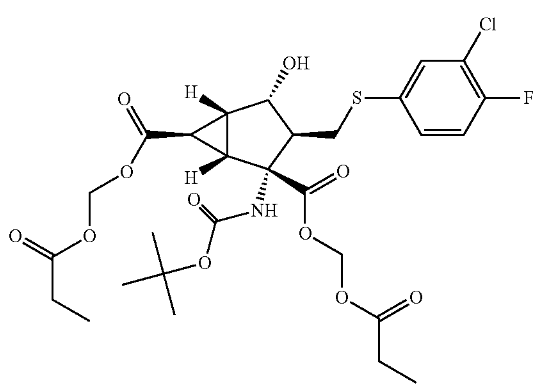 [SMILES: CCC(=O)OCOC(=O)[C@H]1[C@@H]2[C@H](O)[C@@H](CSc3ccc(F)c(Cl)c3)[C@@](NC(=O)OC(C)(C)C)(C(=O)OCOC(=O)CC)[C@H]12] | 28.0 | (M + Na): 670.0 |

EXAMPLE 1

(1S,2R,3S,4S,5R,6R)-2-Amino-3-{[(3,4-difluorophenyl)sulfanyl]methyl}-4-hydroxybicyclo[3.1.0]hexane-2,6-dicarboxylic acid hydrochloride

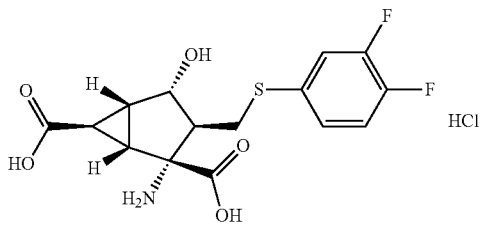 [SMILES: N[C@]1(C(=O)O)[C@@H]2[C@@H](C(=O)O)[C@@H]2[C@H](O)[C@H]1CSc1ccc(F)c(F)c1 ; Cl]

Di-tert-butyl (1S,2R,3S,4S,5R,6R)-2-[(tert-butoxycarbonyl)amino]-3-{[(3,4-difluorophenyl)sulfanyl]methyl}-4-hydroxybicyclo[3.1.0]hexane-2,6-dicarboxylate (0.58 g, 7.19 mmol) is weighed into a 100 mL round bottom with a stir bar. Hydrogen chloride (4N in dioxane, 33 mL, 132.0 mmol) is added. The mixture is warmed to 70° C. for 2 hours and then allowed to cool to ambient temperature. The solvent is removed under reduced pressure to give a residue. The residue is dissolve in dichloromethane (50 mL) and the solvent is removed under reduced pressure to give a residue. This is done three more times to give the title compound (567 mg, 1.43 mmol, 97% yield). MS (m/z): 360.0 (M+1).

The following compounds are prepared essentially by the method of Example 1:

| Ex. No. | Chemical Name | Structure | Yield (%) | Physical Data MS(m/z) |
|---|---|---|---|---|
| 2 | (1S,2R,3S,4S,5R,6R)-2-Amino-3-{[(3-chloro-4-fluorophenyl)sulfanyl]methyl}-4-hydroxybicyclo[3.1.0]hexane-2,6-dicarboxylic acid hydrochloride | 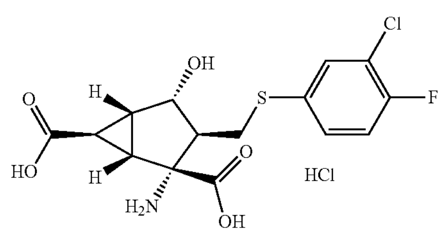 [SMILES: N[C@]1(C(=O)O)[C@@H]2[C@@H](C(=O)O)[C@@H]2[C@H](O)[C@H]1CSc1ccc(F)c(Cl)c1 ; Cl] | 57.1 | (M + H): 376.0 |
| 3 | (1S,2R,3S,4S,5R,6R)-2-Amino-3-{[(4-fluoro-3-methylphenyl)sulfanyl]methyl}-4-hydroxybicyclo[3.1.0]hexane-2,6-dicarboxylic acid hydrochloride | 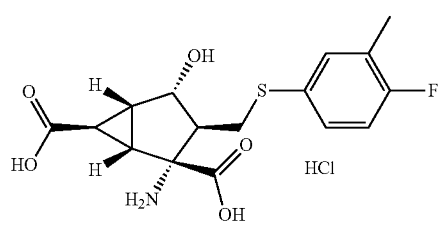 [SMILES: Cc1cc(SC[C@@H]2[C@@H](O)[C@H]3[C@H](C(=O)O)[C@H]3[C@]2(N)C(=O)O)ccc1F ; Cl] | 93.4 | (M + H): 356.0 |
| 4 | (1S,2R,3S,4S,5R,6R)-2-Amino-3-{[(3,4-dichlorophenyl)sulfanyl]methyl}-4-hydroxybicyclo[3.1.0]hexane-2,6-dicarboxylic acid hydrochloride | 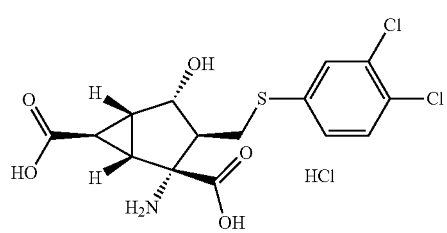 [SMILES: N[C@]1(C(=O)O)[C@@H]2[C@@H](C(=O)O)[C@@H]2[C@H](O)[C@H]1CSc1ccc(Cl)c(Cl)c1 ; Cl] | 101.4 | (M + H): 392.0 |
| 5 | (1S,2R,3S,4S,5R,6R)-2-Amino-3-{[(3-chlorophenyl)sulfanyl]methyl}-4-hydroxybicyclo[3.1.0]hexane-2,6-dicarboxylic acid hydrochloride | 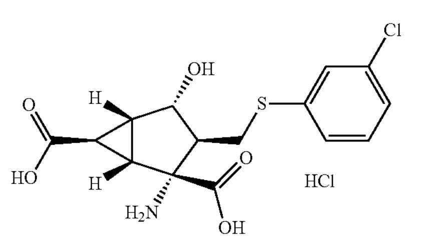 [SMILES: N[C@]1(C(=O)O)[C@@H]2[C@@H](C(=O)O)[C@@H]2[C@H](O)[C@H]1CSc1cccc(Cl)c1 ; Cl] | 82.6 | (M + H): 358.0 |

| Ex. No. | Chemical Name | Structure | Yield (%) | Physical Data MS(m/z) |
|---|---|---|---|---|
| 6 | (1S,2R,3S,4S,5R,6R)-2-Amino-3-{[(4-fluorophenyl)sulfanyl]methyl}-4-hydroxybicyclo[3.1.0]hexane-2,6-dicarboxylic acid hydrochloride | 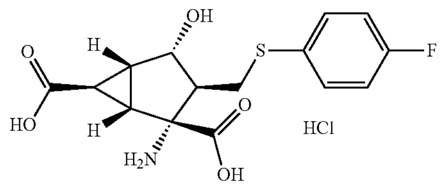 [SMILES: N[C@]1(C(=O)O)[C@@H]2[C@@H](C(=O)O)[C@@H]2[C@H](O)[C@H]1CSc1ccc(F)cc1 ; Cl] | 110.4 | (M + H): 341.8 |
| 7 | (1R,2R,3R,4S,5R,6R)-2-Amino-3-{[(4-fluoro-3-methylphenyl)sulfanyl]methyl}-4-(1H-1,2,4-triazol-3-ylsulfanyl)bicyclo[3.1.0]hexane-2,6-dicarboxylic acid hydrochloride | 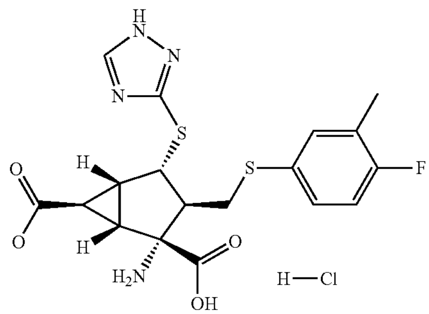 [SMILES: Cc1cc(SC[C@@H]2[C@@H](Sc3nc[nH]n3)[C@H]3[C@H](C(=O)O)[C@H]3[C@]2(N)C(=O)O)ccc1F ; Cl] | 93.0 | (M + H): 438.8 |

EXAMPLE 8

(1S,2R,3S,4S,5R,6R)-2-Amino-4-hydroxy-3-{[(4-methylphenyl)sulfanyl]methyl}bicyclo[3.1.0]hexane-2,6-dicarboxylic acid

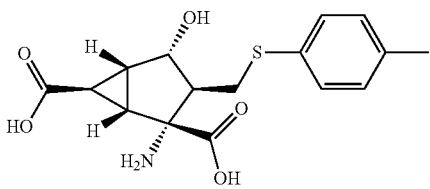 [SMILES: Cc1ccc(SC[C@@H]2[C@@H](O)[C@H]3[C@H](C(=O)O)[C@H]3[C@]2(N)C(=O)O)cc1]

Di-tert-butyl (1S,2R,3S,4S,5R,6R)-2-(tert-butoxycarbonylamino)-4-hydroxy-3-(p-tolylsulfanylmethyl)bicyclo[3.1.0]hexane-2,6-dicarboxylate (300 mg, 545.73 μmol) is placed in a microwave vial. To the vial is added water (2 mL, 110 mmol), and acetic acid (2 mL, 34.9 mmol). The mixture is heated in the microwave to 140° C. for 20 minutes. The solvent is removed under reduced pressure to give the title compound (165 mg, 489.04 μmol, 89.6%). MS (m/z): 338.0 (M+H).

The following compounds are prepared essentially by the method of Example 8:

| Ex. No. | Chemical Name | Structure | Yield (%) | Physical Data MS(m/z) |
|---|---|---|---|---|
| 9 | (1S,2R,3S,4S,5R,6R)-2-Amino-3-{[(3,4-dimethylphenyl)sulfanyl]methyl}-4-hydroxybicyclo[3.1.0]hexane-2,6-dicarboxylic acid | 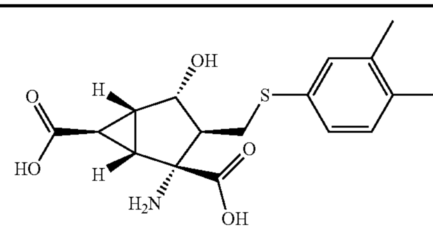 | 96.3 | (M + H): 352.0 |
| 10 | (1S,2R,3R,4S,5R,6S)-4-(Acetylamino)-2-amino-3-{[(4-fluoro-3-methylphenyl)sulfanyl]methyl}bicyclo[3.1.0]hexane-2,6-dicarboxylic acid | 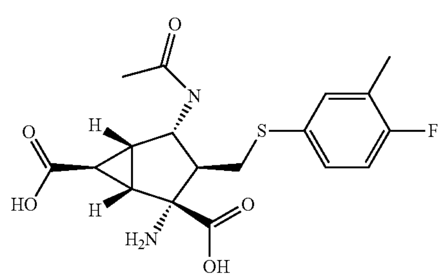 [SMILES: CC(=O)N[C@H]1[C@H]2[C@H](C(=O)O)[C@H]2[C@](N)(C(=O)O)[C@@H]1CSc1ccc(F)c(C)c1] | 93.2 | (M + H): 397.0 |

| Ex. No. | Chemical Name | Structure | Yield (%) | Physical Data MS(m/z) |
|---|---|---|---|---|
| 11 | (1S,2R,3R,4S,5R,6S)-2,4-Diamino-3-{[(4-fluoro-3-methylphenyl)sulfanyl]methyl}bicyclo[3.1.0]hexane-2,6-dicarboxylic acid | 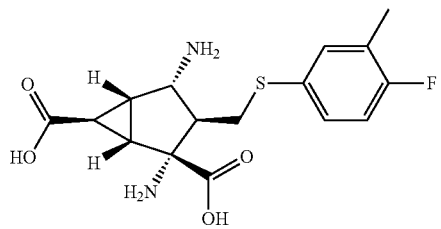 [SMILES: Cc1cc(SC[C@@H]2[C@@H](N)[C@H]3[C@H](C(=O)O)[C@H]3[C@]2(N)C(=O)O)ccc1F] | 84.6 | (M + H): 355.2 |

EXAMPLE 12

Bis({[(1-methylethoxy)carbonyl]oxy}methyl)(1S,2R,3S,4S,5R,6R)-2-amino-3-{[(3,4-difluorophenyl)sulfanyl]methyl}-4-hydroxybicyclo[3.1.0]hexane-2,6-dicarboxylate hydrochloride

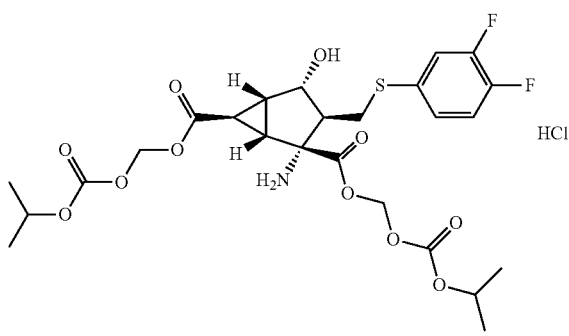 [SMILES: CC(C)OC(=O)OCOC(=O)[C@H]1[C@@H]2[C@H](O)[C@@H](CSc3ccc(F)c(F)c3)[C@@](N)(C(=O)OCOC(=O)OC(C)C)[C@H]12 ; Cl]

Bis({[(1-methylethoxy)carbonyl]oxy}methyl)(1S,2R,3S,4S,5R,6R)-2-[(tert-butoxycarbonyl)amino]-3-{[(3,4-difluorophenyl)sulfanyl]methyl}-4-hydroxybicyclo[3.1.0]hexane-2,6-dicarboxylate (0.88 g, 1.27 mmol) is dissolved in hydrogen chloride (4N in dioxane, 30 mL, 120.00 mmol) and stirred at ambient temperature for 1.5 hours. The solvent is removed under reduced pressure to give a residue. The residue is dissolved in dichloromethane and the solvent removed under reduced pressure. This process is repeated 8 times. The residue is left under high vacuum overnight to give the title compound (0.692 g, 1.10 mmol, 86.61% yield). MS (m/z): 591.8 (M+H).

The following compounds are prepared essentially by the method of Example 12:

| Ex. No. | Chemical Name | Structure | Yield (%) | Physical Data MS(m/z) |
|---|---|---|---|---|
| 13 | Bis{[(2-methylpropanoyl)oxy]methyl}(1S,2R,3S,4S,5R,6R)-2-amino-3-{[(4-fluoro-3-methylphenyl)sulfanyl]methyl}-4-hydroxybicyclo[3.1.0]hexane-2,6-dicarboxylate hydrochloride | 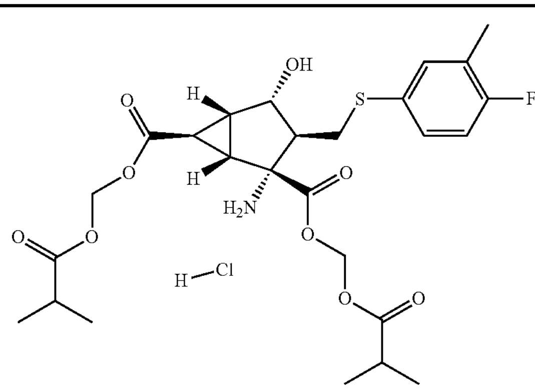 | 90.8 | (M + H): 555.8 |

| Ex. No. | Chemical Name | Structure | Yield (%) | Physical Data MS(m/z) |
|---|---|---|---|---|
| 14 | Bis{[(2-methylpropanoyl)oxy]methyl} (1S,2R,3S,4S,5R,6R)-2-amino-3-{[(3-chloro-4-fluorophenyl)sulfanyl]methyl}-4-hydroxybicyclo[3.1.0]hexane-2,6-dicarboxylate hydrochloride | 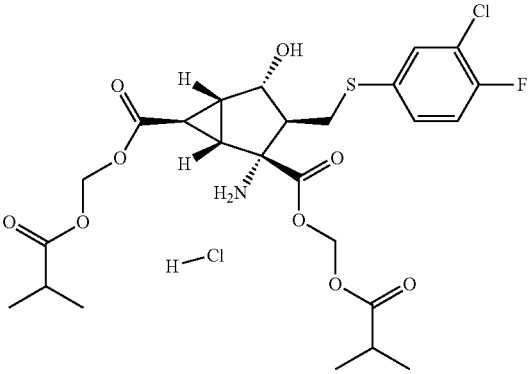 [SMILES: CC(C)C(=O)OCOC(=O)[C@H]1[C@@H]2[C@H](O)[C@@H](CSc3ccc(F)c(Cl)c3)[C@@](N)(C(=O)OCOC(=O)C(C)C)[C@H]12 ; Cl] | 95.5 | (M + H): 575.8 |
| 15 | Bis[(propanoyloxy)methyl] (1S,2R,3S,4S,5R,6R)-2-amino-3-{[(4-fluoro-3-methylphenyl)sulfanyl]methyl}-4-hydroxybicyclo[3.1.0]hexane-2,6-dicarboxylate hydrochloride | 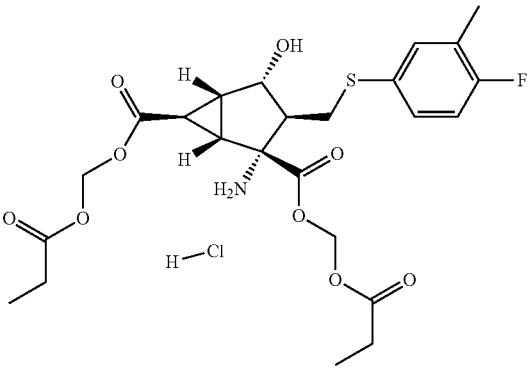 [SMILES: CCC(=O)OCOC(=O)[C@H]1[C@@H]2[C@H](O)[C@@H](CSc3ccc(F)c(C)c3)[C@@](N)(C(=O)OCOC(=O)CC)[C@H]12 ; Cl] | 93.3 | (M + H): 528.0 |
| 16 | Bis[(propanoyloxy)methyl] (1S,2R,3S,4S,5R,6R)-2-amino-3-{[(3-chloro-4-fluorophenyl)sulfanyl]methyl}-4-hydroxybicyclo[3.1.0]hexane-2,6-dicarboxylate hydrochloride | 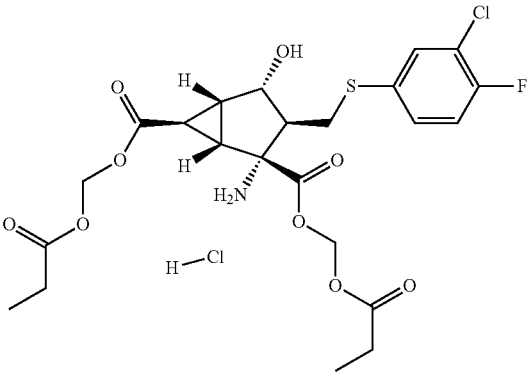 | 55.5 | (M + H): 548.0 |
| 17 | 6-({[(2S)-2-Methylbutanoyl]oxy}methyl) 2-({[(2S)-2-methylbutanoyl]oxy}methyl) (1S,2R,3S,4S,5R,6R)-2-amino-3-{[(4-fluoro-3-methylphenyl)sulfanyl]methyl}-4-hydroxybicyclo[3.1.0]hexane-2,6-dicarboxylate hydrochloride | 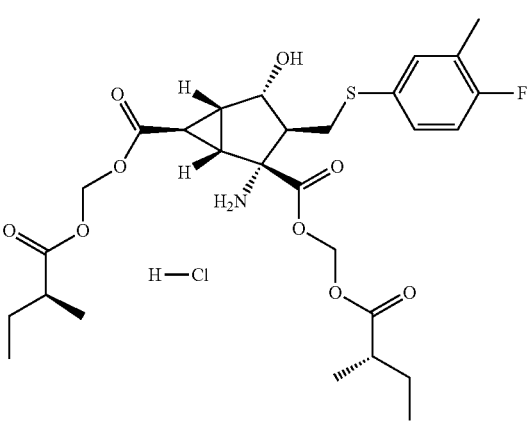 [SMILES: CC[C@H](C)C(=O)OCOC(=O)[C@H]1[C@@H]2[C@H](O)[C@@H](CSc3ccc(F)c(C)c3)[C@@](N)(C(=O)OCOC(=O)[C@@H](C)CC)[C@H]12 ; Cl] | 68.2 | (M + H): 584.0 |

| Ex. No. | Chemical Name | Structure | Yield (%) | Physical Data MS(m/z) |
|---|---|---|---|---|
| 18 | Bis{[(cyclopentylcarbonyl)oxy]methyl} (1S,2R,3S,4S,5R,6R)-2-amino-3-{[(4-fluoro-3-methylphenyl)sulfanyl]methyl}-4-hydroxybicyclo[3.1.0]hexane-2,6-dicarboxylate hydrochloride | 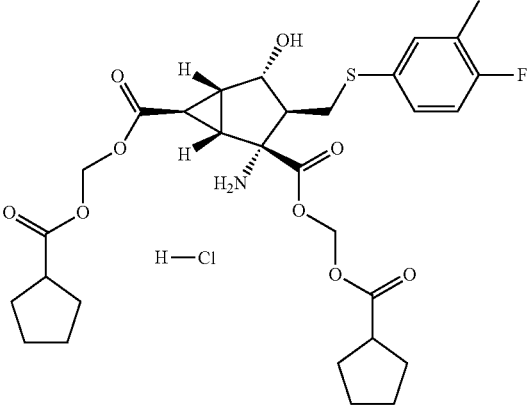 [SMILES: Cc1cc(SC[C@@H]2[C@@H](O)[C@H]3[C@H](C(=O)OCOC(=O)C4CCCC4)[C@H]3[C@]2(N)C(=O)OCOC(=O)C2CCCC2)ccc1F ; Cl] | 71 | (M + H): 608.2 |
| 19 | Bis{[(ethoxycarbonyl)oxy]methyl} (1S,2R,3S,4S,5R,6R)-2-amino-3-{[(3,4-dimethylphenyl)sulfanyl]methyl}-4-hydroxybicyclo[3.1.0]hexane-2,6-dicarboxylate hydrochloride | 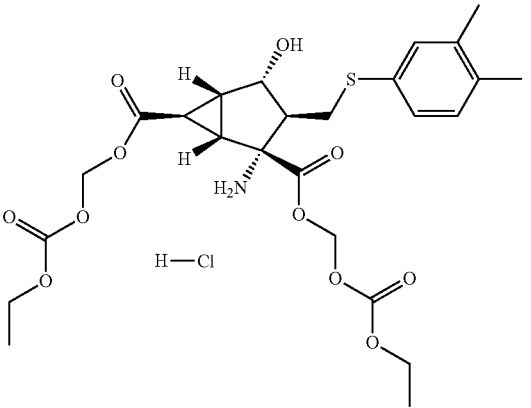 [SMILES: CCOC(=O)OCOC(=O)[C@H]1[C@@H]2[C@H](O)[C@@H](CSc3ccc(C)c(C)c3)[C@@](N)(C(=O)OCOC(=O)OCC)[C@H]12 ; Cl] | 79.4 | (M + H): 556.2 |
| 20 | Bis{[(2-methylpropanoyl)oxy]methyl} (1S,2R,3S,4S,5R,6R)-2-amino-3-{[(3,4-difluorophenyl)sulfanyl]methyl}-4-hydroxybicyclo[3.1.0]hexane-2,6-dicarboxylate hydrochloride | 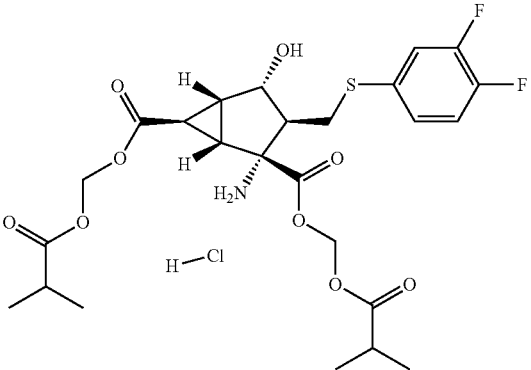 [SMILES: CC(C)C(=O)OCOC(=O)[C@H]1[C@@H]2[C@H](O)[C@@H](CSc3ccc(F)c(F)c3)[C@@](N)(C(=O)OCOC(=O)C(C)C)[C@H]12 ; Cl] | 89.7 | (M + H): 560.2 |

-continued

| Ex. No. | Chemical Name | Structure | Yield (%) | Physical Data MS(m/z) |
|---|---|---|---|---|
| 21 | Bis{[(ethoxycarbonyl)oxy]methyl} (1S,2R,3S,4S,5R,6R)-2-amino-3-{[(4-fluorophenyl)sulfanyl]methyl}-4-hydroxybicyclo[3.1.0]hexane-2,6-dicarboxylate hydrochloride | 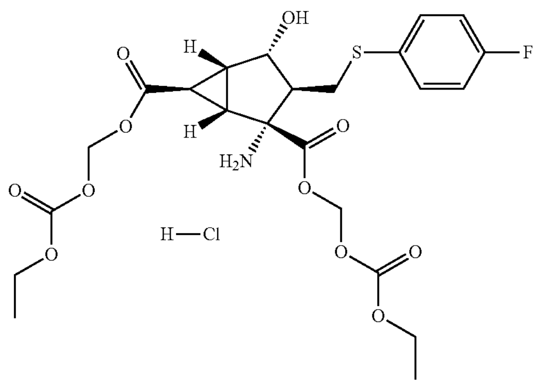 [SMILES: CCOC(=O)OCOC(=O)[C@H]1[C@@H]2[C@H](O)[C@@H](CSc3ccc(F)cc3)[C@@](N)(C(=O)OCOC(=O)OCC)[C@H]12 ; Cl] | 89.5 | (M + H): 546.2 |
| 22 | Bis({[(1-methylethoxy)carbonyl]oxy}methyl) (1S,2R,3S,4S,5R,6R)-2-amino-3-{[(3-chloro-4-fluorophenyl)sulfanyl]methyl}-4-hydroxybicyclo[3.1.0]hexane-2,6-dicarboxylate hydrochloride | 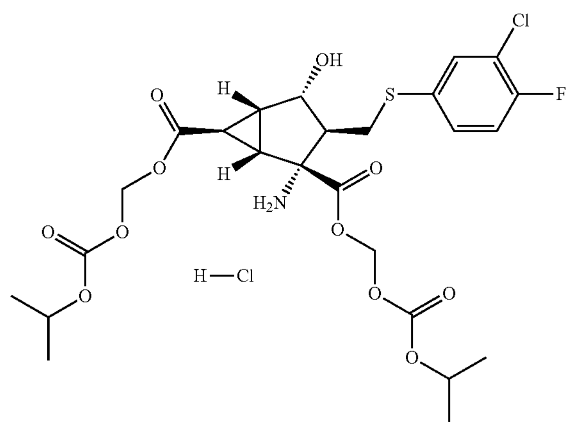 [SMILES: CC(C)OC(=O)OCOC(=O)[C@H]1[C@@H]2[C@H](O)[C@@H](CSc3ccc(F)c(Cl)c3)[C@@](N)(C(=O)OCOC(=O)OC(C)C)[C@H]12 ; Cl] | 100 | (M + H): 607.8 |
| 23 | Bis({[(1-methylethoxy)carbonyl]oxy}methyl) (1S,2R,3S,4S,5R,6R)-2-amino-3-{[(4-fluoro-3-methylphenyl)sulfanyl]methyl}-4-hydroxybicyclo[3.1.0]hexane-2,6-dicarboxylate hydrochloride | 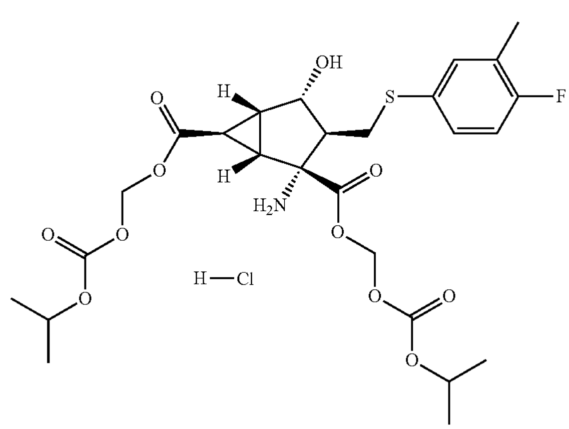 [SMILES: Cc1cc(SC[C@@H]2[C@@H](O)[C@H]3[C@H](C(=O)OCOC(=O)OC(C)C)[C@H]3[C@]2(N)C(=O)OCOC(=O)OC(C)C)ccc1F ; Cl] | 101.5 | (M + H): 587.8 |

-continued

| Ex. No. | Chemical Name | Structure | Yield (%) | Physical Data MS(m/z) |
|---|---|---|---|---|
| 24 | Bis{[(2-ethylbutanoyl)oxy]methyl} (1S,2R,3S,4S,5R,6R)-2-amino-3-{[(4-fluoro-3-methylphenyl)sulfanyl]methyl}-4-hydroxybicyclo[3.1.0]hexane-2,6-dicarboxylate hydrochloride | 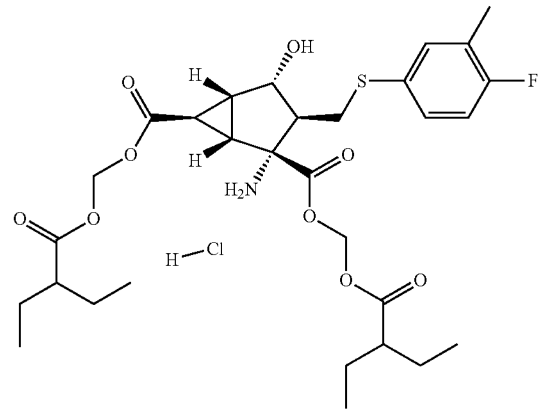 | 36.5 | (M + H): 612.0 |
| 25 | Bis{[(3-methylbutanoyl)oxy]methyl} (1S,2R,3S,4S,5R,6R)-2-amino-3-{[(4-fluoro-3-methylphenyl)sulfanyl]methyl}-4-hydroxybicyclo[3.1.0]hexane-2,6-dicarboxylate hydrochloride | 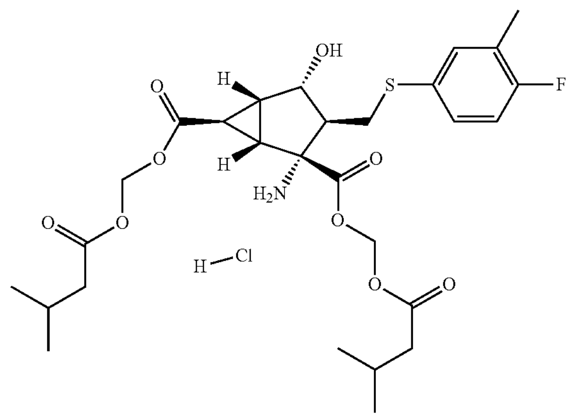 [SMILES: Cc1cc(SC[C@@H]2[C@@H](O)[C@H]3[C@H](C(=O)OCOC(=O)CC(C)C)[C@H]3[C@]2(N)C(=O)OCOC(=O)CC(C)C)ccc1F ; Cl] | 36.1 | (M + H): 584.2 |
| 26 | Bis[(acetyloxy)methyl] (1S,2R,3S,4S,5R,6R)-2-amino-3-{[(4-fluoro-3-methylphenyl)sulfanyl]methyl}-4-hydroxybicyclo[3.1.0]hexane-2,6-dicarboxylate hydrochloride | 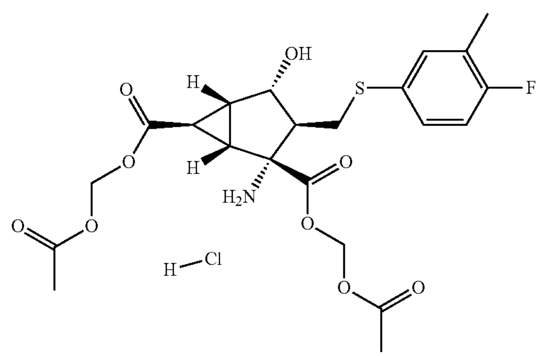 [SMILES: CC(=O)OCOC(=O)[C@H]1[C@@H]2[C@H](O)[C@@H](CSc3ccc(F)c(C)c3)[C@@](N)(C(=O)OCOC(C)=O)[C@H]12 ; Cl] | 84.6 | (M + H): 500.0 |
| 27 | Bis[(acetyloxy)methyl] (1S,2R,3S,4S,5R,6R)-2-amino-3-{[(3-chloro-4-fluorophenyl)sulfanyl]methyl}-4-hydroxybicyclo[3.1.0]hexane-2,6-dicarboxylate hydrochloride | 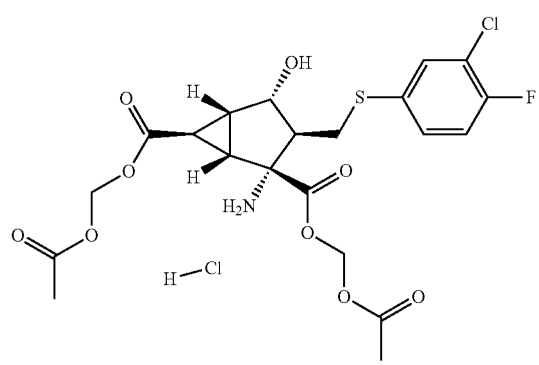 [SMILES: CC(=O)OCOC(=O)[C@H]1[C@@H]2[C@H](O)[C@@H](CSc3ccc(F)c(Cl)c3)[C@@](N)(C(=O)OCOC(C)=O)[C@H]12 ; Cl] | 94.7 | (M + H): 520.0 |

| Ex. No. | Chemical Name | Structure | Yield (%) | Physical Data MS(m/z) |
|---|---|---|---|---|
| 28 | Bis{[(cyclopropylcarbonyl)oxy]methyl} (1S,2R,3S,4S,5R,6R)-2-amino-3-{[(4-fluoro-3-methylphenyl)sulfanyl]methyl}-4-hydroxybicyclo[3.1.0]hexane-2,6-dicarboxylate hydrochloride | 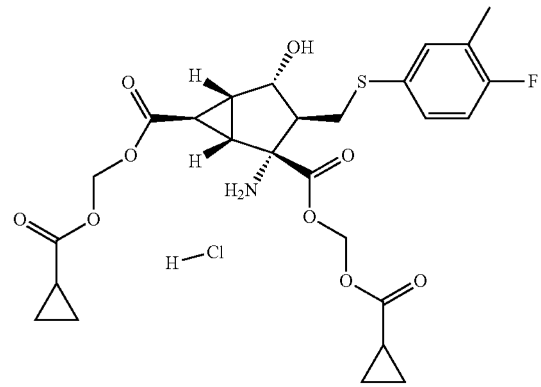 [SMILES: Cc1cc(SC[C@@H]2[C@@H](O)[C@H]3[C@H](C(=O)OCOC(=O)C4CC4)[C@H]3[C@]2(N)C(=O)OCOC(=O)C2CC2)ccc1F ; Cl] | 79.2 | (M + H): 552.2 |
| 29 | Bis{[(ethoxycarbonyl)oxy]methyl} (1S,2R,3S,4S,5R,6R)-2-amino-3-{[(3,4-difluorophenyl)sulfanyl]methyl}-4-hydroxybicyclo[3.1.0]hexane-2,6-dicarboxylate hydrochloride | 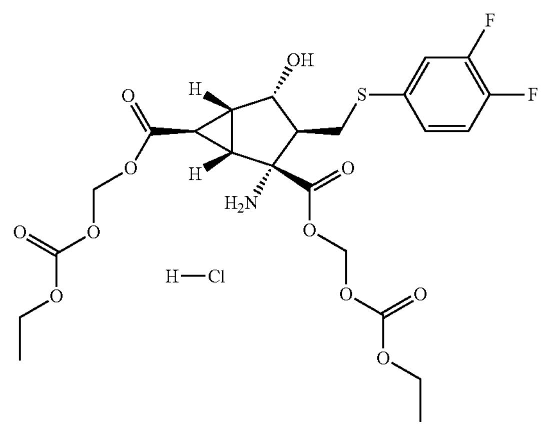 | 96.2 | (M + H): 564.2 |
| 30 | Bis{[(ethoxycarbonyl)oxy]methyl} (1S,2R,3S,4S,5R,6R)-2-amino-3-{[(4-fluoro-3-methylphenyl)sulfanyl]methyl}-4-hydroxybicyclo[3.1.0]hexane-2,6-dicarboxylate hydrochloride | 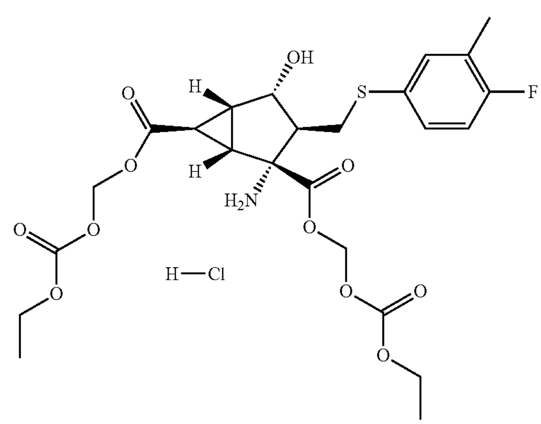 [SMILES: CCOC(=O)OCOC(=O)[C@H]1[C@@H]2[C@H](O)[C@@H](CSc3ccc(F)c(C)c3)[C@@](N)(C(=O)OCOC(=O)OCC)[C@H]12 ; Cl] | 96.2 | (M + H): 560.2 |

| Ex. No. | Chemical Name | Structure | Yield (%) | Physical Data MS(m/z) |
|---|---|---|---|---|
| 31 | Bis{[(ethoxycarbonyl)oxy]methyl} (1S,2R,3S,4S,5R,6R)-2-amino-3-{[(3-chloro-4-fluorophenyl)sulfanyl]methyl}-4-hydroxybicyclo[3.1.0]hexane-2,6-dicarboxylate hydrochloride | 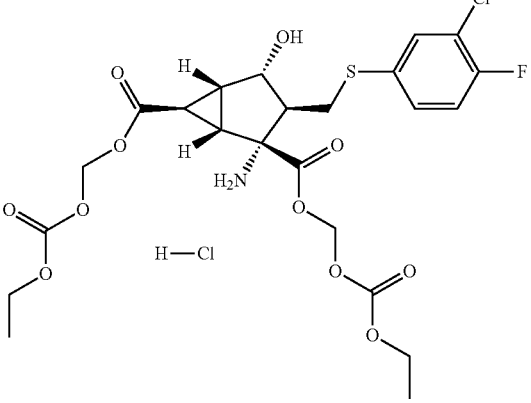 | 95.1 | (M + H): 580.0 |

EXAMPLE 32

Bis({[(1-methylethoxy)carbonyl]oxy}methyl)(1S,2R,3S,4S,5R,6R)-2-amino-3-{[(3,4-difluorophenyl)sulfanyl]methyl}-4-hydroxybicyclo[3.1.0]hexane-2,6-dicarboxylate hydrochloride

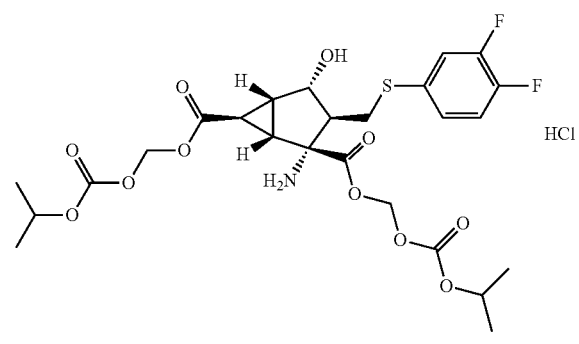 [SMILES: CC(C)OC(=O)OCOC(=O)[C@H]1[C@@H]2[C@H](O)[C@@H](CSc3ccc(F)c(F)c3)[C@@](N)(C(=O)OCOC(=O)OC(C)C)[C@H]12 ; Cl]

STEP 1: Ditert-butyl (1S,2R,5R,6R)-2-(tert-butoxycarbonylamino)-3-(dimethylaminomethylene)-4-oxo-bicyclo[3.1.0]hexane-2,6-dicarboxylate

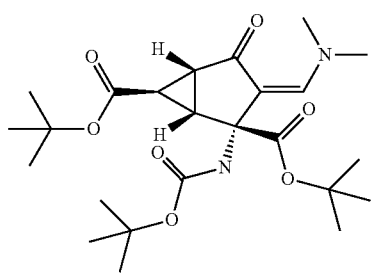 [SMILES: CN(C)/C=C1\C(=O)[C@H]2[C@H](C(=O)OC(C)(C)C)[C@H]2[C@]1(NC(=O)OC(C)(C)C)C(=O)OC(C)(C)C]

Tert-butoxybis(dimethylamino)methane (481.1 ml, 2.33 mol) is added to a suspension of di-tert-butyl(1S,2S,5R,6R)-2-[(tert-butoxycarbonyl)amino]-4-oxobicyclo[3.1.0]hexane-2,6-dicarboxylate (600 g, 1.46 mol) in dry toluene (3.6 L) at room temperature under nitrogen. The mixture is heated at 80° C. for 3 hour and 45 minutes, then cooled to room temperature and stirred overnight. The reaction volume is reduced in vacuo, diluted with methyl tert-butyl ether (1.8 L) and hexane (1.8 L), and stirred for 3 hours at 15° C. After 3 hours, the resulting solid is collected by filtration, washed with cold hexane (2×1.8 L), and dried under vacuum to obtain the title compound (620.4 g, yield 91%). HPLC-MS: 98%.

STEP 2: Di-tert-butyl (1S,2R,5R,6R)-2-[(tert-butoxycarbonyl)amino]-3-methylidene-4-oxobicyclo[3.1.0]hexane-2,6-dicarboxylate

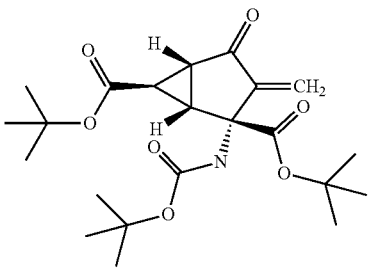 [SMILES: C=C1C(=O)[C@H]2[C@H](C(=O)OC(C)(C)C)[C@H]2[C@]1(NC(=O)OC(C)(C)C)C(=O)OC(C)(C)C]

To a solution of di-tert-butyl (1S,2R,5R,6R)-2-(tert-butoxycarbonylamino)-3-(dimethylaminomethylene)-4-oxo-bicyclo[3.1.0]hexane-2,6-dicarboxylate (620.4 g, 1.33 mol) in dry tetrahydrofuran (12 L), triethylamine (277.3 ml, 1.99 mol) is added at room temperature under nitrogen. The mixture is cooled to −47° C. and diisobutylaluminum hydride (1M in hexane, 2.06 L, 2.06 mol) is added dropwise over 2 hours. The resulting mixture is stirred at −47° C. After 1 hour 15 minutes, acetic acid (118 ml, 2.06 mol) is dropwise added at −47° C., warmed to room temperature, and then stirred overnight. Add 20% $H_3PO_4$ in water until pH=2. Separate the organic phase and extract the aqueous phase with ethyl acetate (2×1.7 L). The combined organic phases are washed successively with 10% aqueous HCl (1.5 L), water (1.5 L), and brine (1.5 L), dried over anhydrous sodium sulfate, filtered, and concentrated to yield a solid. The resulting solid is triturated with water (3.2 L), collected by filtration, and then dried to yield the title compound (558.2 g, yield 99%). HPLC-MS: 97.4%.

STEP 3: Di-tert-butyl (1S,2R,3S,5R,6R)-2-[(tert-butoxycarbonyl)amino]-3-{[(3,4-difluorophenyl)sulfanyl]methyl}-4-oxobicyclo[3.1.0]hexane-2,6-dicarboxylate

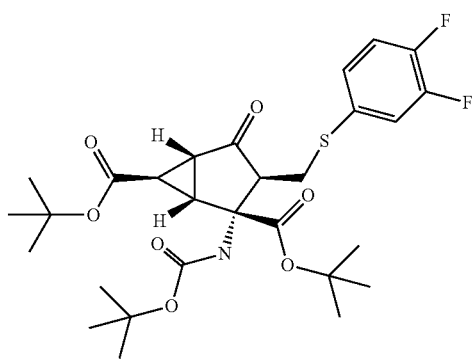 [SMILES: CC(C)(C)OC(=O)N[C@]1(C(=O)OC(C)(C)C)[C@@H]2[C@@H](C(=O)OC(C)(C)C)[C@@H]2C(=O)[C@H]1CSc1ccc(F)c(F)c1]

A suspension of di-tert-butyl (1S,2R,5R,6R)-2-[(tert-butoxycarbonyl)amino]-3-methylidene-4-oxobicyclo[3.1.0]hexane-2,6-dicarboxylate (350.00 g, 826.43 mmol) in toluene (2.95 L) is treated with 3,4-difluorobenzenethiol (172.49 g, 1.18 mol) and triethylamine (205.61 mL, 149.28 g, 1.48 mol) at 25° C. The mixture is stirred at 80° C. After twelve hours, the reaction was cooled to room temperature, washed sequentially with 2N aqueous NaOH (pH=10) and aqueous. 1N HCl (pH=4), dried over MgSO₄, and concentrated in vacuo to yield a residue. Triturate the residue with hexane (1 L) and remove the solvent to yield the title compound (664 g, 100% yield).

STEP 4: Di-tert-butyl (1S,2R,3S,4S,5R,6R)-2-[(tert-butoxycarbonyl)amino]-3-{[(3,4-difluorophenyl)sulfanyl]methyl}-4-hydroxybicyclo[3.1.0]hexane-2,6-dicarboxylate

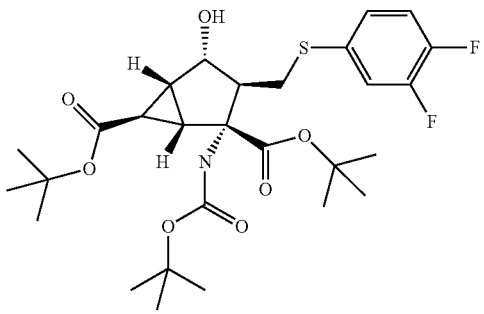 [SMILES: CC(C)(C)OC(=O)N[C@]1(C(=O)OC(C)(C)C)[C@@H]2[C@@H](C(=O)OC(C)(C)C)[C@@H]2[C@H](O)[C@H]1CSc1ccc(F)c(F)c1]

A solution of 1N(R)-methyl oxazaborolidine in toluene (228.21 mL) and borane-methyl sulfide complex (86.68 g, 101.98 mL, 1.14 mol) in anhydrous methyl t-butyl ether (4.56 L) is cooled to −40° C. ° C. To this solution, di-tert-butyl (1S,2R,3S,5R,6R)-2-[(tert-butoxycarbonyl)amino]-3-{[(3,4-difluorophenyl)sulfanyl]methyl}-4-oxobicyclo[3.1.0]hexane-2,6-dicarboxylate (650.00 g, 1.14 mol) in methyl t-butyl ether (3.42 L) is added via addition funnel over 2 hours whereupon the reaction is warmed to 0° C. After 1 hour, methanol (461.80 mL, 11.41 mol) is added, and internal temperature is kept below 15° C. The reaction is washed with 2N aqueous. NaOH (2 L), dried over MgSO₄, and concentrated in vacuo to yield a residue. The residue is purified by silica gel chromatography (8:1 to 1:1 hexane/ethyl acetate) to yield the title compound (580 g, 89% yield).

STEP 5: (1S,2R,3S,4S,5R,6R)-2-Amino-3-{[(3,4-difluorophenyl)sulfanyl]methyl}-4-hydroxybicyclo[3.1.0]hexane-2,6-dicarboxylic acid

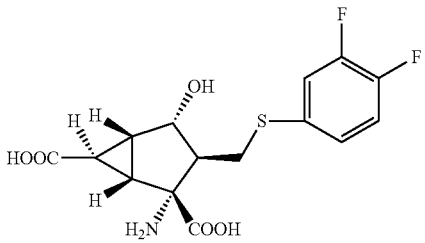 [SMILES: N[C@]1(C(=O)O)[C@@H]2[C@@H](C(=O)O)[C@@H]2[C@H](O)[C@H]1CSc1ccc(F)c(F)c1]

Water (1.10 L) and 12.18M hydrogen chloride in water (789.88 mL, 9.62 mol) is added to a solution of di-tert-butyl (1S,2R,3S,4S,5R,6R)-2-[(tert-butoxycarbonyl)amino]-3-{[(3,4-difluorophenyl)sulfanyl]methyl}-4-hydroxybicyclo[3.1.0]hexane-2,6-dicarboxylate (550.00 g, 962.07 mmol) in 1,4-dioxane (192.41 mL). The resulting slurry is stirred at 100° C. After 12 hours, the reaction is then cooled to 25° C., stirred for 12 hours, and then basified with NaOH (50% wt/wt) to pH=2.65. The resulting mixture is stirred at 10° C. for 30 minutes whereupon the precipitate is collected by filtration, washed with water (1 L) and methyl tert-butyl ether (1 L), and dried for 2 hours at 25° C., and then at 60° C. in a oven until constant weight to yield the title compound (300 g, 87% yield). MS (m/z): 360 (M+1).

Step 6: (1S,2R,3S,4S,5R,6R)-2-[(tert-butoxycarbonyl)amino]-3-{[(3,4-difluorophenyl)sulfanyl]methyl}-4-hydroxybicyclo[3.1.0]hexane-2,6-dicarboxylic acid

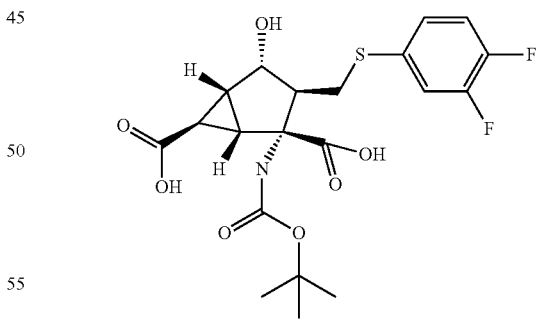

Triethylamine (407.27 mL, 2.92 mol) and [2-(tert-butoxycarbonyloxyimino)-2-phenylacetonitrile] (308.39 g, 1.25 mol) are added to a suspension of (1S,2R,3S,4S,5R,6R)-2-amino-3-{[(3,4-difluorophenyl)sulfanyl]methyl}-4-hydroxybicyclo[3.1.0]hexane-2,6-dicarboxylic acid (300.00 g, 834.84 mmol) in 1,4-dioxane (500.9 mL) and water (500.9 mL) at 25° C. The mixture is warmed to 50° C. After 12 hours, the reaction is cooled to 25° C., diluted with water (2.5 L), and washed with methyl tert-butyl ether (6×1 L). Basify the aqueous phase with a solution of aqueous. 1N HCl until pH=2, and extract with ethyl acetate (3×2 L). The combined ethyl acetate extracts are washed with brine, dried over MgSO$_4$, and concentrated in vacuo to yield the title compound (250 g, 65% yield). MS (m/z): 360 (M+-Boc).

STEP 7: Bis({[(1-methylethoxy)carbonyl]oxy}methyl)(1S,2R,3S,4S,5R,6R)-2-[(tert-butoxycarbonyl)amino]-3-{[(3,4-difluorophenyl)sulfanyl]methyl}-4-hydroxybicyclo[3.1.0]hexane-2,6-dicarboxylate

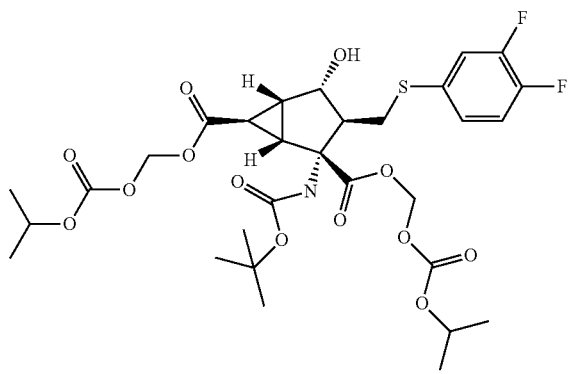 [SMILES: CC(C)OC(=O)OCOC(=O)[C@H]1[C@@H]2[C@H](O)[C@@H](CSc3ccc(F)c(F)c3)[C@@](NC(=O)OC(C)(C)C)(C(=O)OCOC(=O)OC(C)C)[C@H]12]

A solution of (1S,2R,3S,4S,5R,6R)-2-[(tert-butoxycarbonyl)amino]-3-{[(3,4-difluorophenyl)sulfanyl]methyl}-4-hydroxybicyclo[3.1.0]hexane-2,6-dicarboxylic acid (150.00 g, 326.46 mmol) in dimethylformamide (3.38 L) is successively treated with potassium carbonate (1 180.48 g, 1.31 mo), chloromethyl isopropyl carbonate (149.43 g, 979.39 mmol), and sodium iodide (9.79 g, 65.29 mmol), and the mixture is stirred under nitrogen at 25° C. After 12 hours, water (1.5 L) is added to the mixture, solids are filtered off, and filtrate is extracted with methyl tert-butyl ether (3×1.5 L). The combined organics are washed with successively with water, brine, dried over MgSO$_4$, and concentrated in vacuo. The resulting residue is purified by silica gel chromatography (2:1 to 1:1 hexane/ethyl acetate) to afford the title compound (225 g, 70% yield). MS (m/z): 592 (M+-Boc).

STEP 8: Bis({[(1-methylethoxy)carbonyl]oxy}methyl)(1S,2R,3S,4S,5R,6R)-2-amino-3-{[(3,4-difluorophenyl)sulfanyl]methyl}-4-hydroxybicyclo[3.1.0]hexane-2,6-dicarboxylate hydrochloride

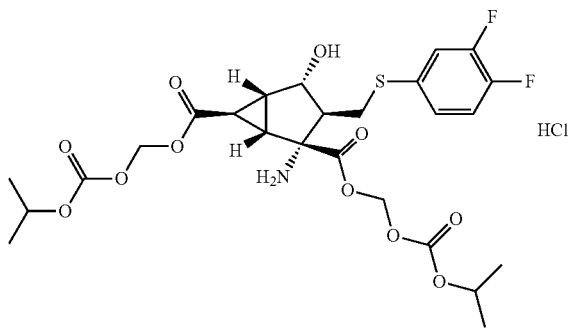 [SMILES: CC(C)OC(=O)OCOC(=O)[C@H]1[C@@H]2[C@H](O)[C@@H](CSc3ccc(F)c(F)c3)[C@@](N)(C(=O)OCOC(=O)OC(C)C)[C@H]12 ; Cl]

Bis({[(1-methylethoxy)carbonyl]oxy}methyl)(1S,2R,3S,4S,5R,6R)-2-[(tert-butoxycarbonyl)amino]-3-{[(3,4-difluorophenyl)sulfanyl]methyl}-4-hydroxybicyclo[3.1.0]hexane-2,6-dicarboxylate (124.9 g, 180.57 mmol) is treated with 4N hydrogen chloride in 1,4-dioxane (1.12 L, 4.50 mol) at 25° C. After 90 minutes, solvent was removed in vacuo, and the residue is slurried in methyl tert-butyl ether (1 L) for 30 minutes. The resulting precipitate is collected by filtration, washed with methyl tert-butyl ether (500 mL), and dried in an oven at 45° C. for 16 hours. The resulting salt is dissolved in dichloromethane and water then neutralized with triethylamine. The organic phase is separated, dried over MgSO$_4$, and concentrated in vacuo to yield a residue. The residue is purified by silica gel chromatography (3:1 to 1:1 hexane/ethyl acetate), to yield the free base which is treated with 4N HCl in 1,4-dioxane (950 mL) at 25° C. After 15 minutes, the solvent is evaporated in vacuo, and residue is slurried in methyl tert-butyl ether (1 L) and hexanes (250 mL). The resulting solid is filtered, washed with methyl tert-butyl ether (500 mL), and dried in vacuo at 45° C. until constant weight to provide the title compound (98.5 g, 87% yield). MS (m/z): 592 (M+1).

Literature data (Witkin, Jeffrey M., and Eiler, William J. A. (2006), *Antagonism of Metabotropic Glutamate Group II Receptors in the Potential Treatment of Neurological and Neuropsychiatric Disorders*. Drug Development Research vol 67, pg. 757-769; and Yasuhara, Akito and Chaki, Shigeyuki, (2010) *Metabotropic Glutamate Receptors: Potential Drug Targets for Psychiatric Disorders*, The Open Medicinal Chemistry Journal, vol. 4, pg. 20-36.) and data generated in non-clinical animal studies support a role for mGlu2/3 antagonists in the treatment of depressive disorders and disorders of excessive sleepiness. Specifically it is found that mGlu 2/3 receptor antagonists are effective in rodent models of depressive disorders and promote wakefulness using EEG monitored rodents without disproportionate or clinically relevant hyperactivity or overwhelming compensatory hypersomnolence. The increased alertness manifests in increased attention, improved cognitive performance, and a likelihood of reduced fatigue. As the previously described disorders represent common co-morbid clinical conditions, an mGlu2/3 receptor antagonist may be particularly effective in specific patient populations, such as patients with major depressive disorder, treatment refractory depression, unipolar depression, dysthymia, and/or cyclothimia, or any disorders of excessive sleepiness. Disorders of excessive sleepiness may include, but are not limited to excessive daytime sleepiness (EDS), hypersomnia associated with obstructive sleep apnea or narcolepsy, circadian rhythm sleep disorders (including, but not limited to shift work sleep disorder, jet lag disorder, delayed sleep phase disorder, advanced phase sleep disorder, and non-24 hour sleep-wake syndrome), idiopathic hypersomnolance and excessive sleepiness associated with non-restorative sleep (NRS)

To further demonstrate the characteristics of the present compounds, representative compounds may be run in the following in vitro and in vivo assays:

mGlu2 and mGlu3 Receptor cAMP Antagonist Assays

Antagonist activity is assayed in recombinant AV12 cells stably expressing human mGlu2 or mGlu3 receptors and the rat glutamate transporter EAAT1 (Excitatory Amino Acid Transporter 1). The cell lines are maintained by culturing in DMEM with high glucose and pyridoxine hydrochloride supplemented with 5% dialyzed fetal bovine serum (FBS), 1 mM sodium pyruvate, 1 mM HEPES and 1 mM L-glutamine; geneticin and hygromycin B are used as selection antibiotics. Confluent cultures are grown at 37° C. in an atmosphere containing 6.5% CO$_2$, and passaged biweekly. Cells are harvested using 0.25% trypsin, suspended in freeze media (FBS with 10% DMSO) at $10^7$ cells/ml, and aliquots are stored in liquid nitrogen. Twenty-four hours before the assay, cells are plated at a density of 8,000-10,000 cells per well in a tissue culture treated, 96-well, half-area black plates (Costar 3875) in 50 µl of DMEM with high glucose and pyridoxine hydrochloride supplemented with 5% dialyzed FBS, 1 mM sodium pyruvate, 1 mM HEPES, 100 µg/ml ampicillin, and 250 µM (mGlu2) or 125 µM (mGlu3) of L-glutamine.

Reversal of the inhibition of forskolin-stimulated cAMP production by test compounds is measured using homogeneous time resolved fluorescence technology (HTRF; Cisbio cat #62AM4PEB). The medium is removed and the cells are incubated with 100 µl cAMP stimulation buffer (STIM) for 30 minutes at 37° C. (STIM buffer contains 500 ml HBSS, 1000 ml DPBS, 0.034% BSA, 1.67 mM HEPES and 500 µM IBMX (Sigma I5879).) Compounds are tested in 10-point concentration response curves using 3× serial dilution followed by further 40-fold dilution into STIM buffer. DCG IV (Tocris 0975) serves as the reference agonist. The final reaction mixture contains 1 µM (for mGlu2) or 3 µM (for mGlu3) of forskolin (Sigma F6886), DCG IV at its $EC_{90}$, and up to 25 µM of test compound. Cells are incubated at 37° C. for 20 minutes. To measure the cAMP levels, cAMP-d2 conjugate and anti cAMP-cryptate conjugate in lysis buffer are incubated with the treated cells at room temperature for 1 hour (mGlu2) or 1.5 hour (mGlu3). The HTRF signal is detected using an EnVision plate reader (Perkin-Elmer) to calculate the ratio of fluorescence at 665 to 620 nM. The raw data are converted to cAMP amount (pmole/well) using a cAMP standard curve generated for each experiment. Relative $IC_{50}$ values are calculated from the top-bottom range of the concentration response curve using a four-parameter logistic curve fitting program (ActivityBase v5.3.1.22).

FLIPR and cAMP Assays for mGlu Receptor Selectivity

The relative antagonist potencies of the compounds of the invention for the other human mGlu receptors can be assessed with either a cAMP assay or fluorometric calcium response assay (see for example Fell et al., JPET (in press)). Briefly, individual AV12 cell lines containing the rat EAAT1 glutamate transporter and stably expressing the human mGlu1, 2, 3, 4, 5, 6, & 8 receptors are used for these studies. The mGlu1 and 5 receptors are Gq-coupled, so they naturally signal through phospholipase C, producing a calcium flux response which can be used to measure receptor activation using a Fluorometric Imaging Plate Reader (FLIPR, Molecular Devices). The cell lines expressing the mGlu2, 3, 4, and 8 receptor are designed to express the Gα15 subunit so that these Gi-coupled receptors will generate a calcium flux response similar to the mGlu1 and 5 receptor expressing cell lines. The mGlu6 receptor is tested in a cAMP format using methods analogous to those developed for mGlu2 and mGlu3 above. These cell lines are maintained as previously described except that amounts of L-glutamine and selection agents (geneticin, hygromycin B, zeocin, and blasticidin) may vary depending on the cell line. Confluent cultures are passaged biweekly.

Intracellular calcium levels are monitored using FLIPR before and after the addition of test compounds and Fluo-3 AM (Invitrogen) or Calcium 4 (Molecular Devices) dye, depending on the cell line. Cells are plated 24 hours prior to assay in a variable concentration of glutamine and a variable density of cells per well, depending on the cell line. The medium is removed and the cells are incubated with 8 µM of dye (50 µl per well) for 90 or 120 minutes (depending on cell line) at 25° C. A single-addition FLIPR assay generating an 11-point concentration response curve for the agonist glutamate is conducted prior to each experiment to confirm the appropriate sensitivity of the cells. The results are analyzed using GraphPad Prism v4.03 to calculate the concentrations of glutamate needed to induce the $EC_{90}$ (antagonist assay) and $EC_{10}$ (potentiator assay) responses.

Compounds are tested at each mGlu receptor in a two-addition FLIPR assay using a 10-point concentration response profile starting at a final concentration of 25 µM for the agonist assay and 12.5 µM for the potentiator and antagonist assays. The first addition detects any agonist activity, and the second addition consists of 100 µl of select concentrations (depending on cell line) of glutamate in assay buffer generating an $EC_{10}$ or $EC_{90}$ glutamate response. Agonist effects are quantified as percent stimulation induced by compound alone relative to the maximal glutamate response. Antagonist effects are quantified by calculating the percent inhibition of the $EC_{90}$ glutamate response caused by the compound. Potentiation effects are quantified as percent increase in the presence of an $EC_{10}$ response in glutamate relative to the $EC_{max}$ response. All data are calculated as relative $IC_{50}$ or $EC_{50}$ values using a four-parameter logistic curve fitting program (ActivityBase v5.3.1.22).

Antagonist activity in mGlu6 cells is measured using cAMP in a method analogous to that described above for mGlu2 and mGlu3 activity, except that the reference agonist was L-AP4 (Tocris). To measure mGlu6 agonist activity, the extent to which the compound inhibits the forskolin-stimulated cAMP production is calculated. Relative $IC_{50}$ and $EC_{50}$ values are calculated from the top-bottom range of the concentration response curve using a four-parameter logistic curve fitting program (ActivityBase v5.3.1.22).

Exemplified compounds wherein $R^1$ and $R^2$ are both hydrogen are tested essentially as described above and are found to have high antagonist potency for the mGlu2 and mGlu3 receptors. The exemplified compounds wherein $R^1$ and $R^2$ are both hydrogen are also found to be selective antagonists of the mGlu2 and mGlu3 receptors as against other mGlu receptor subtypes. $IC_{50}$'s for the mGlu2 and mGlu3 receptors for the exemplified compounds wherein $R^1$ and $R^2$ are both hydrogen are found to be less than 70 nM and 140 nM, respectively, while the $IC_{50}$'s for other mGlu receptors tested are found to be significantly greater. The compounds of examples 1 and 2 are tested essentially as described above and are found to have activity profiles as shown in Table 1.

TABLE 1

| | Selectivity data | | | | | | |
|---|---|---|---|---|---|---|---|
| Ex. | mGlu1 % inhib. @12.5 µM | mGlu2 IC50 nM | mGlu3 IC50 nM | mGlu4 % inhib. @12.5 µM | mGlu5 % inhib. @12.5 µM | mGlu6 IC50 nM | mGlu8 % inhib. @12.5 µM |
| 1 | 6.3% | 15.4 ± 2.0 | 6.2 ± 2.2 | 17.9% | −2.0% | 1720 | 47.0% ($IC_{50}$ 4970 nM) |

TABLE 1-continued

| | Selectivity data | | | | | | |
|---|---|---|---|---|---|---|---|
| Ex. | mGlu1 % inhib. @12.5 µM | mGlu2 IC50 nM | mGlu3 IC50 nM | mGlu4 % inhib. @12.5 µM | mGlu5 % inhib. @12.5 µM | mGlu6 IC50 nM | mGlu8 % inhib. @12.5 µM |
| 2 | 7.9% | 12.7 ± 2.3 | 13.4 ± 3.4 | 28.0% | 21.4% | 1395 | 68.7% ($IC_{50}$ 7860 nM) |

Further, certain compounds of the present invention show a lack of significant activity at other physiologically important receptors such as, but not limited to, the hERG channel, serotonin receptors (specifically $5-HT_{2A}$ and $5-HT_{2B}$), muscarinic receptors (specifically M2), and iGluR receptors (specifically iGluR5). The compound of example 1 is tested using known assay methods and is found to have no appreciable activity at these receptors.

Therefore, physiologically relevant doses of the compounds of the invention are expected to provide substantial inhibition of mGlu2 and mGlu3 receptors in vivo, while not substantially interacting with other mGlu receptors, or other physiologically relevant receptors, and thus are expected to provide the desired pharmacology while avoiding undesired effects associated with off-target activity.

Forced-Swim Test in Mice (mFST)

mFST is an established in vivo assay for antidepressant activity (Li et al. *J Pharmacol Exp Ther.* 319(1):254-9, 2006). Mice treated with known clinically effective antidepressants (selective serotonin reuptake inhibitors and/or tricyclic antidepressants) exhibit the behavior of reduced time spent immobile after being placed in a water tank, a behavior associated with despair. The mFST was used to evaluate potential antidepressant-like activity of novel mGlu2/3 antagonists essentially as described in previously published methods (see for example, Li et al. *J Pharmacol Exp Ther.* 319(1):254-9, 2006). Briefly, male NIH-Swiss mice (Harlan Sprague-Dawley, Indianapolis, Ind.) weighing between 25-30 g are used. Group housed animals are removed from the vivarium to the testing area in their own cages and allowed to adapt to the new environment for at least 1 hour before testing. Compounds where $R^1$ and $R^2$ are both hydrogen are dissolved in water with minimal NaOH added for dissolution and are administered i.p. Compounds where $R^1$ and/or $R^2$ are other than hydrogen are prepared on the day of use in 2.0-2.5% N-methyl-pyrrolidinone and then suspended in 1% HEC, 0.25% Tween 80, and 0.05% Dow antifoam, and administered orally. Mice are placed in a cylinder (diameter: 10 cm; height: 25 cm) filled with 6 cm of water (22-25° C.) for 6 min. The duration of immobility during the last 4 min. of the 6 min. period of the test was scored. A mouse is recorded as immobile when floating motionless or making only those movements necessary to keep its head above water.

Representative compounds are tested essentially as described above and are found to significantly reduce immobilization times in wild type mice. Exemplified compounds wherein $R^1$ and $R^2$ are both hydrogen are assayed essentially as described above and are found to have $ED_{60}$'s less than 30 mg/kg i.p., with maximal decreases in immobilization times of at least 25%. The compounds of Examples 1, 2, 12/32 and 22 are assayed essentially as described above and are found to have activities as shown in Table 2. Therefore compounds of the present invention are expected to have antidepressant activity in vivo.

TABLE 2

| Mouse Forced Swim Test (mFST) | | |
|---|---|---|
| Example | $ED_{60}$ (mg/kg) | Maximal Decrease (1 − compound/control) * 100% |
| 1 | 8.0 (i.p.) | 36.1% |
| 2 | 24.5 (i.p.) | 33.5% |
| 12/32 | 12.0 (p.o.) | 58.4% |
| 22 | 20.5 (p.o.) | 50.1% |

In other experiments, mice with receptor deletions (mGlu2 knock-out mice) are studied; these mice are bred by heterozygote×heterozygote breeding and used as littermates for −/− and +/+ mouse comparisons (Taconic Farms). The compounds of examples 1 and 2 (10 mg/kg, i.p., 30 min prior) are found to significantly decrease immobility time in mGlu2+/+ mice, but not in mGlu2−/− mice. Similarly, the compound of example 12/32 (30 mg/kg, po, 120 min prior) is found to decrease immobility time in mGlu2+/+ mice, but not in mGlu2−/− mice. These findings further demonstrate that the mGlu2 receptor contributes to the antidepressant-like effects of the compounds of the invention.

The compounds of the invention may also be tested in combination with other compounds useful for the treatment of depressive disorders, as for example SSRI's, for their ability to enhance the antidepressant-like effects over that of either compound alone. The compound of example 12 (10 mg/kg p.o.) is tested in the mouse forced swim test alone and in combination with either fluoxetine (10 mg/kg, i.p.) or citalopram (1 mg/kg, i.p.) and found to significantly increase the antidepressant-like effect over that of either compound alone as shown in Table 3, below. Further, testing of brain and plasma levels of the active di-acid moiety of the compound of example 12 (i.e. the same compound as the freebase of example 1), and plasma levels of fluoxetine and citalopram, show no increase in exposure levels, supporting the finding that the increased antidepressant-like activity was not due merely to an increase in central exposure to the compounds.

TABLE 3

| mFST with SSRI | | | |
|---|---|---|---|
| Compound(s) | Immobilization Time (sec.) | Std error of mean | Maximal Decrease (1 − compound/control) * 100% |
| Vehicle | 173 | 14 | |
| Example 12 | 130 | 17 | 24.5% |
| Fluoxetine | 118 | 16 | 31.5% |
| Ex. 12 + Fluoxetine | 80 | 15 | 53.6%* |
| Vehicle | 176 | 14 | |
| Example 12 | 140 | 8 | 20.9% |
| Citalopram | 102 | 18 | 42.1% |
| Ex. 12 + Citalopram | 80 | 13 | 54.8%** |

*Significantly different from either compound of Example 12 or fluoxetine alone, $p < 0.05$
**Significantly different from either compound of Example 12 or citalopram alone, $p < 0.05$ Wakefulness and Behavioral Monitoring in Rats:

Representative compounds of the present invention are tested in rats for their ability to increase the amount of time in a state of wakefulness without undesired effects such as inhibition of REM sleep, waking motor impairment (disproportionate hyper- or hypolocomotion), and/or rebound hypersomnia Test animals are continuously monitored by electroencephalograms (EEG), electromyograms (EMG), and motion to measure cumulative time awake, rebound hypersomnia, and locomotor activity intensity during wakefulness. Methods for such studies are known in the art (see for example methods described in Edgar D M, Seidel W F. Modafinil induces wakefulness without intensifying motor activity or subsequent rebound hypersomnolence in the rat. *J Pharmacology & Experimental Therapeutics* 1997; 283: 757-769; van Gelder R N, Edgar D M, Dement W C. Real-time automated sleep scoring: validation of a microcomputer-based system for mice. *Sleep* 1991, 14: 48-55; and Gross B A, Walsh C M, Turakhia A A, Booth V, Mashour G A, Poe G R. Open-source logic-based automated sleep scoring software using electrophysiological recordings in rats. *J Neurosci Methods*. 2009; 184(1):10-8.) Studies are conducted as follows:

Animal Preparation.

Adult, male Wistar rats (approximately 270-300 g at time of surgery) are surgically fitted for chronic recording of EEG, EMG, body temperature, and motion as follows: Rats are surgically prepared with a cranial implant consisting of four stainless steel screws for EEG recording (two frontal [3.9 mm anterior from bregma, and ±2.0 mm mediolaterally] and two occipital [6.4 mm posterior from bregma, ±5.5 mm mediolaterally]), and with two Teflon-coated stainless steel wires for EMG recording (positioned under the nuchal trapezoid muscles). All leads are soldered to a miniature connector (Microtech, Boothwyn, Pa.) prior to surgery. The implant assembly is affixed to the skull by the combination of the stainless steel EEG recording screws, cyanoacrylate applied between the implant connector and skull, and dental acrylic. Body temperature and locomotor activity is monitored via a miniature transmitter (Minimitter PDT4000G, Philips Respironics, Bend, Oreg.) surgically placed into the abdomen. At least 3 weeks are allowed for recovery.

Recording Environment.

Each rat is housed individually within a microisolator cage modified with an inserted polycarbonate filter-top riser to allow more vertical headroom. A flexible cable that minimally restricts movement is connected at one end to a commutator affixed to the cage top and at the other end to the animal's cranial implant. Each cage is located within separate, ventilated compartments of a stainless steel sleep-wake recording chamber. Food and water are available ad libitum and the ambient temperature is maintained at about 23±1° C. A 24-hr light-dark cycle (LD 12:12) using fluorescent light is maintained throughout the study. Relative humidity averages approximately 50%. Animals are undisturbed for at least 30 hrs before and after each treatment.

Study Design and Dosing.

Compounds where $R^1$ and $R^2$ are both hydrogen are dissolved in water with minimal NaOH added for dissolution and are administered i.p in a volume of 1.0 mL per kg body weight. Compounds where $R^1$ and/or $R^2$ are other than hydrogen are administer p.o. in a volume of 2 mL per kg body weight in one of two alternative vehicles: i) 2.5% N-methyl-2-pyrrolidinone in hydroxyethylcellulose; or ii) 10% acacia with 0.05% Dow Corning® Antifoam in water. The vehicle or one of the compound dose levels is administered pseudo-randomly such that no rat receives the same treatment twice, and no rat receives more than two of the 8 treatments in any one study. Each rat is removed from its cage for about a minute to be weighed and treated. At least 6 days "washout" period precede and follow each treatment.

Data Collection.

Sleep and wakefulness discrimination may be automated (e.g., Van Gelder et al. 1991; Edgar et al. 1997, Winrow et al., 2010; Gross et al., 2009). EEG is amplified and filtered (×10,000, bandpass 1-30 Hz), EMG is amplified and integrated (bandpass 10-100 Hz, RMS integration), and non-specific locomotor activity (LMA) is monitored simultaneously. Arousal states are classified in 10 second epochs as non-REM sleep, REM sleep, wakefulness, or theta-dominated wakefulness. Locomotor activity (LMA) is recorded as counts per minute and is detected by commercially available telemetry receivers (ER4000, Minimitter, Bend, Oreg.).

Statistical Analysis.

Ages and body weights are summarized by mean, minimum and maximum over the treatment groups. All animals having at least one outcome are included in the summary results (for example, we include appropriate data from an animal treatment for which telemetry data are usable but EEG data are not). The post-treatment observation period is divided into 2 post-dosing intervals (the first 7 hours, and the first 19 hours) where the time of dosing is defined as the start of Hour=0. The outcomes are summarized in each period by computing either the mean hourly or the cumulative value across each period. Each outcome in each period is analyzed by analysis of covariance using treatment group and treatment date as factors and the corresponding pre-treatment interval, 24 hrs earlier, as the covariate. Adjusted means and the change from vehicle means and their corresponding standard errors are summarized for each treatment group. Adjusted Dunnett's multiple-comparison P values are shown for each outcome in each period. Not all outcomes are analyzed in all periods, as shown in Table 1, which thus affect the experiment-wise type I error rate. As such, no further adjustments are made for multiple testing.

Determining Efficacy.

The threshold efficacious dose is estimated as the lowest dose for which cumulative time awake exceeds 50 minutes relative to vehicle controls across the first 7 hours post-treatment. A finer determination may be made by conducting subsequent studies of more closely spaced doses around the efficacious dose.

Determining Undesired Effects.

Two potentially undesired effects in particular are evaluated: rebound hypersomnolence and intensified motor activity (Edgar D M, Seidel W F, 1997).

(i) Rebound hypersomnolence may be measured as decreased levels of wakefulness during the period 8-19 hours after efficacious treatment doses. A biologically significant decrease is defined as a greater than 50 percent of the cumulative increase during the first 7 hours. Thus, if wakefulness increased by 100 minutes during the first 7 hours, then a decrease in cumulative wakefulness of 50 minutes or more, relative to vehicle controls, during the period 8-19 hours after treatment would be deemed biologically significant. Group mean changes, shown in Table 2, show a lack of rebound hypersomnolence.

(ii) Intensified motor activity is defined as an average increase relative to vehicle controls that exceeds 5 LMA counts per minute of EEG-defined wakefulness at the efficacy threshold dose, and for which the effect is dose related. Group mean increases in Table 2 were all under 5 counts per minute of wakefulness and are not dose dependent.

Exemplified compounds are tested essentially as described and are found to promote wakefulness without significant rebound hypersomnia or intensified motor activity. Exemplified compounds where $R^1$ and $R^2$ are both hydrogen (administered i.p.) are tested essentially as described and are found to be efficacious at doses of 10 mg/kg or lower. The compound of Example 12 is tested essentially as described and is found to have the cumulative time awake profile and locomotor activity intensity as shown in Table 4.

TABLE 4

| Dose (mg/kg PO) | N | Mean | SE | P |
|---|---|---|---|---|
| Cumulative Time Awake first 7 hours | | | | |
| 60 | 12 | 118.9 | 14.3 | <0.0001 |
| 30 | 12 | 109.3 | 14.1 | <0.0001 |
| 10 | 9 | 40.2 | 15.6 | 0.0368 |
| Cumulative Time Awake 8-19 hours | | | | |
| 60 | 12 | 2.7 | 14.4 | 0.8535 |
| 30 | 12 | −4.1 | 14.5 | 0.7760 |
| 10 | 9 | 12.1 | 16.0 | 0.4546 |
| Locomotor Activity Intensity (note 1) | | | | |
| 60 | 7 | 4.9 | 2.0 | 0.0191 |
| 30 | 12 | 3.0 | 1.8 | 0.0939 |
| 10 | 6 | 4.5 | 2.0 | 0.0349 |

Outcome statistics:
Mean values represent the difference from vehicle controls.
SE = standard error of the mean;
P = P-value adjusted for multiple contrasts for the efficacy variable. Unadjusted P values are shown for 'undesired effect' measures (Cumulative Time Awake 8-19 hours, and Locomotor Activity Intensity). Cumulative time awake given in minutes.
(note 1). Locomotor activity (LMA) intensity = counts of LMA per minute of EEG-defined wakefulness, averaged over the first 7 hr post-treatment.

Additionally, in three separate experiments, mice with single mGlu2(−/−), single mGlu3(−/−), or double mGlu2 (−/−) mGlu3(−/−) receptor deletions are studied. These mice are bred by heterozygote×heterozygote breeding and used as littermates for −/− and +/+ mouse comparisons (Taconic Farms). The compound of example 1 (10 mg/kg, i.p.) is found to significantly increase wakefulness in wild type mice, single knockout mGlu3(−/−) mice, and single knockout mGlu2(−/−) mice, though at a reduced level. In contrast, the compound of example 1 is found to not significantly increase wakefulness in the double knockout mGlu2(−/−) mGlu3(−/−) mice. These findings demonstrate that both the mGlu2 and mGlu3 receptors contribute to the wake-promoting effect of the compounds of the invention.

While it is possible to administer compounds employed in the methods of this invention directly without any formulation, the compounds are usually administered in the form of pharmaceutical compositions comprising at least one compound of Formula I, or a pharmaceutically acceptable salt thereof, as an active ingredient and at least one pharmaceutically acceptable carrier, diluent and/or excipient. These compositions can be administered by a variety of routes including oral, sublingual, nasal, subcutaneous, intravenous, and intramuscular. Such pharmaceutical compositions and processes for preparing them are well known in the art. See, e.g., Remington: The Science and Practice of Pharmacy (University of the Sciences in Philadelphia, ed., 21$^{st}$ ed., Lippincott Williams & Wilkins Co., 2005). Compounds of Formula I where $R^1$ or $R^2$ or both are other than hydrogen are preferred for oral administration to improve bioavailability, whereas Compounds of Formula I where $R^1$ and $R^2$ are both hydrogen are preferred for i.v., i.p., or intramuscular administration.

The compositions are preferably formulated in a unit dosage form, each dosage containing from about 1 to about 600 mg, more usually about 30 to about 300 mg, as for example between about 50 and about 250 mg of the active ingredient. The term "unit dosage form" refers to physically discrete units suitable as unitary dosages for human subjects and other mammals, each unit containing a predetermined quantity of active material calculated to produce the desired therapeutic effect, in association with at least one suitable pharmaceutically acceptable carrier, diluent and/or excipient.

The compounds of Formula I are generally effective over a wide dosage range. For example, dosages per day normally fall within the range of about 0.01 to about 10 mg/kg, more usually from about 0.3 to 5.0 mg/kg, and as for example between 0.5 and 3.0 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. A compound of the formula

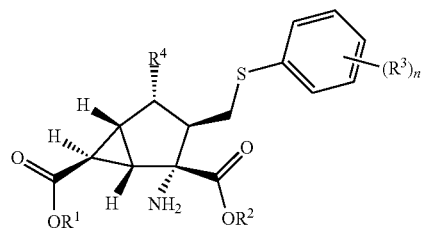

where $R^1$ and $R^2$ are each independently hydrogen, $C_1$-$C_3$ alkoxycarbonyloxymethyl, $C_1$-$C_5$ alkylcarbonyloxymethyl, or $C_{3-6}$ cycloalkylcarbonyloxymethyl;
$R^3$ is independently at each occurrence methyl, fluoro, or chloro;
$R^4$ is hydroxyl, amino, methylcarbonylamino, or 1,2,4-triazolylthio; and
n is 1 or 2;
or a pharmaceutically acceptable salt thereof.

2. The compound according to claim 1 where $R^1$ and $R^2$ are each hydrogen, or a pharmaceutically acceptable salt thereof.

3. The compound according to claim 1 where $R^1$ and $R^2$ are both other than hydrogen, or a pharmaceutically acceptable salt thereof.

4. The compound according to claim 1 where $R^1$ and $R^2$ are the same and are other than hydrogen, or a pharmaceutically acceptable salt thereof.

5. The compound according to claim 4 where $R^1$ and $R^2$ are each isopropyloxycarbonyloxymethyl, or a pharmaceutically acceptable salt thereof.

6. The compound according to claim 1 where n is 2 and the $R^3$ groups are at the phenyl 3- and 4-positions, or a pharmaceutically acceptable salt thereof.

7. The compound according to claim 1 where $R^3$ is independently at each occurrence chloro or fluoro, or a pharmaceutically acceptable salt thereof.

8. The compound according to claim 1 which is (1S,2R, 3S,4S,5R,6R)-2-amino-3-{[(3,4-difluorophenyl)sulfanyl]

methyl}-4-hydroxybicyclo[3.1.0]hexane-2,6-dicarboxylic acid, or a pharmaceutically acceptable salt thereof.

9. The compound according to claim 1 which is bis({[(1-methylethoxy)carbonyl]oxy}methyl)(1S,2R,3S,4S,5R,6R)-2-amino-3-{[(3,4-difluorophenyl)sulfanyl]methyl}-4-hydroxybicyclo[3.1.0]hexane-2,6-dicarboxylate, or a pharmaceutically acceptable salt thereof.

10. The compound according to claim 1 which is (1S,2R,3S,4S,5R,6R)-2-amino-3-{[(3-chloro-4-fluorophenyl)sulfanyl]methyl}-4-hydroxybicyclo[3.1.0]hexane-2,6-dicarboxylic acid, or a pharmaceutically acceptable salt thereof.

11. The compound according to claim 1 which is bis({[(1-methylethoxy)carbonyl]oxy}methyl)(1S,2R,3S,4S,5R,6R)-2-amino-3-{[(3-chloro-4-fluorophenyl)sulfanyl]methyl}-4-hydroxybicyclo[3.1.0]hexane-2,6-dicarboxylate, or a pharmaceutically acceptable salt thereof.

12. A pharmaceutical composition comprising a compound according to claim 1, or a pharmaceutically acceptable salt thereof, in combination with at least one pharmaceutically acceptable carrier, excipient or diluent.

13. The pharmaceutical composition according to claim 12, wherein the compound is (1S,2R,3S,4S,5R,6R)-2-amino-3-{[(3,4-difluorophenyl)sulfanyl]methyl}-4-hydroxybicyclo[3.1.0]hexane-2,6-dicarboxylic acid, or a pharmaceutically acceptable salt thereof.

14. The pharmaceutical composition according to claim 12, wherein the compound is bis({[(1-methylethoxy)carbonyl]oxy}methyl)(1S,2R,3S,4S,5R,6R)-2-amino-3-{[(3,4-difluorophenyl)sulfanyl]methyl}-4-hydroxybicyclo[3.1.0]hexane-2,6-dicarboxylate, or a pharmaceutically acceptable salt thereof.

15. The pharmaceutical composition according to claim 12, wherein the compound is (1S,2R,3S,4S,5R,6R)-2-amino-3-{[(3-chloro-4-fluorophenyl)sulfanyl]methyl}-4-hydroxybicyclo[3.1.0]hexane-2,6-dicarboxylic acid, or a pharmaceutically acceptable salt thereof.

16. The pharmaceutical composition according to claim 12, wherein the compound is bis({[(1-methylethoxy)carbonyl]oxy}methyl)(1S,2R,3S,4S,5R,6R)-2-amino-3-{[(3-chloro-4-fluorophenyl)sulfanyl]methyl}-4-hydroxybicyclo[3.1.0]hexane-2,6-dicarboxylate, or a pharmaceutically acceptable salt thereof.

17. A method for treating depressive disorders in a mammal comprising administering to a mammal in need of such treatment an effective amount of a compound according to claim 1, or a pharmaceutically acceptable salt thereof.

18. The method of claim 17 where the mammal is a human.

19. A method for treating disorders of excessive sleepiness in a mammal comprising administering to a mammal in need of such treatment an effective amount of a compound according to claim 1, or a pharmaceutically acceptable salt thereof.

20. The method of claim 19 where the mammal is a human.

21. A method for treating depressive disorders in a mammal comprising administering to a mammal in need of such treatment an effective amount of a compound according to claim 1, or a pharmaceutically acceptable salt thereof, in simultaneous, separate or sequential combination with a serotonin reuptake inhibitor.

22. The method of claim 21 wherein the serotonin reuptake inhibitor is fluoxetine or citalopram.

23. The method of claim 21 wherein the mammal is a human.

24. The method of claim 22 wherein the mammal is a human.

\* \* \* \* \*

UNITED STATES PATENT AND TRADEMARK OFFICE
CERTIFICATE OF CORRECTION

PATENT NO. : 8,629,169 B2  
APPLICATION NO. : 13/296384  
DATED : January 14, 2014  
INVENTOR(S) : Stephon Cornell Smith et al.

Page 1 of 1

It is certified that error appears in the above-identified patent and that said Letters Patent is hereby corrected as shown below:

Title Page, Column 2, References Cited (Other Publications), Line 11: Delete "Trituium" and insert -- Tritium --, therefor.

Signed and Sealed this  
Thirteenth Day of May, 2014

Michelle K. Lee  
*Deputy Director of the United States Patent and Trademark Office*